US011291989B2

(12) United States Patent
Morrison

(10) Patent No.: US 11,291,989 B2
(45) Date of Patent: Apr. 5, 2022

(54) METHODS AND DEVICES FOR SAMPLE COLLECTION AND STABILIZATION

(71) Applicant: Labrador Diagnostics LLC, Healdsburg, CA (US)

(72) Inventor: Zachary Morrison, San Francisco, CA (US)

(73) Assignee: Labrador Diagnostics LLC, Wilmington, DE (US)

( * ) Notice: Subject to any disclaimer, the term of this patent is extended or adjusted under 35 U.S.C. 154(b) by 435 days.

(21) Appl. No.: 16/308,416

(22) PCT Filed: May 5, 2017

(86) PCT No.: PCT/US2017/031411
§ 371 (c)(1),
(2) Date: Dec. 7, 2018

(87) PCT Pub. No.: WO2017/193076
PCT Pub. Date: Nov. 9, 2017

(65) Prior Publication Data
US 2019/0210014 A1    Jul. 11, 2019

Related U.S. Application Data

(60) Provisional application No. 62/333,137, filed on May 6, 2016.

(51) Int. Cl.
| | | |
|---|---|---|
| *B01L 3/00* | (2006.01) | |
| *A61B 5/151* | (2006.01) | |
| *A61B 5/15* | (2006.01) | |

(52) U.S. Cl.
CPC ............... *B01L 3/502* (2013.01); *A61B 5/15* (2013.01); *A61B 5/151* (2013.01);
(Continued)

(58) Field of Classification Search
CPC ............... B01L 3/502; B01L 3/50825; B01L 2300/044; B01L 2200/026; B01L 2300/042; B01L 2300/0838; B01L 2300/16; B01L 2400/049; A61B 5/151; A61B 5/15; A61B 5/150099; A61B 5/150213; A61B 5/150351
See application file for complete search history.

(56) References Cited

U.S. PATENT DOCUMENTS

| | | |
|---|---|---|
| 3,645,252 A | 2/1972 | Gilford |
| 4,974,603 A | 12/1990 | Jacobs |
| (Continued) | | |

OTHER PUBLICATIONS

International Search Report dated Aug. 24, 17 for PCT/US2017/031411.

*Primary Examiner* — Jennifer Wecker
*Assistant Examiner* — Jonathan Bortoli

(57) ABSTRACT

Methods and devices are provided for sample collection. In one example, a device is provided comprising at least one capillary tube or collection channel directed to a sample vessel, wherein in a one-step removal step of detaching the sample vessel from the collection channel, a vacuum force is created within the sample vessel, due in part of the pulling of the sealed vessel away from the device, wherein this vacuum force draw out residual sample that may still be resident in the collection channel.

13 Claims, 20 Drawing Sheets

(52) U.S. Cl.
CPC .. *A61B 5/150099* (2013.01); *A61B 5/150213* (2013.01); *A61B 5/150351* (2013.01); *B01L 3/50825* (2013.01); *B01L 2200/026* (2013.01); *B01L 2300/042* (2013.01); *B01L 2300/044* (2013.01); *B01L 2300/0838* (2013.01); *B01L 2300/16* (2013.01); *B01L 2400/049* (2013.01)

(56) References Cited

U.S. PATENT DOCUMENTS

| | | |
|---|---|---|
| 5,891,105 A | 4/1999 | Mahurkar |
| 7,883,476 B2* | 2/2011 | Miller ................ A61B 10/0275 600/587 |
| 2012/0123297 A1 | 5/2012 | Brancazio |
| 2014/0050620 A1* | 2/2014 | Johnson ........... A61B 5/150755 422/68.1 |
| 2014/0342371 A1* | 11/2014 | Holmes ............ A61B 5/150786 435/6.12 |
| 2020/0337620 A1 | 10/2020 | Morrison et al. |

* cited by examiner

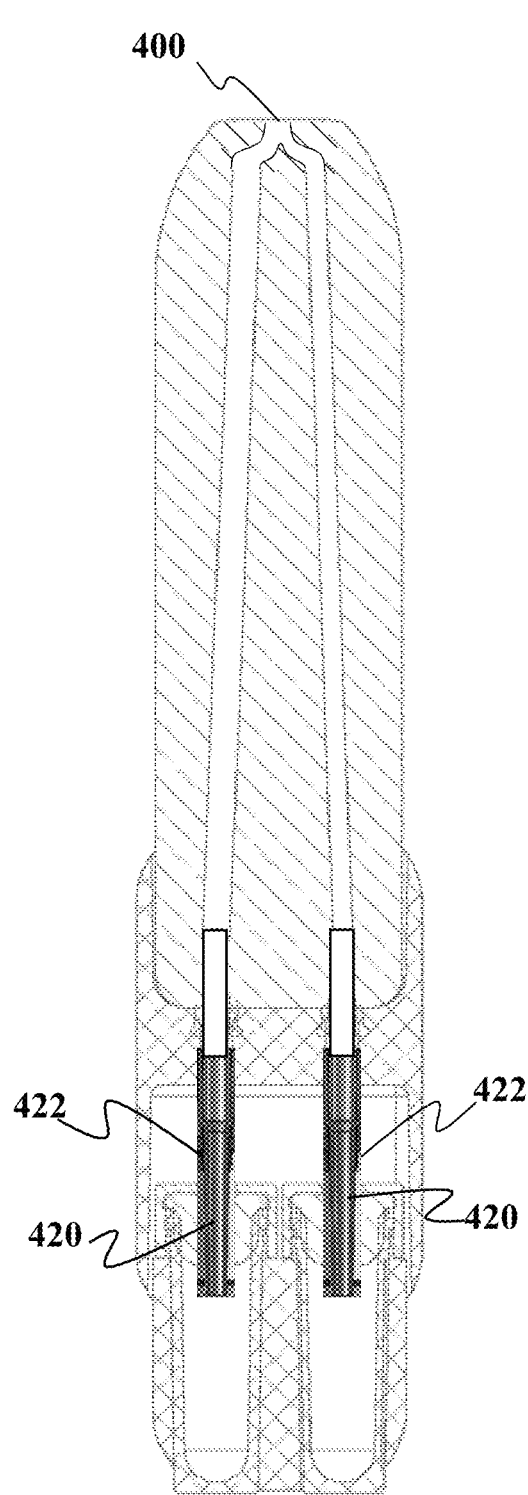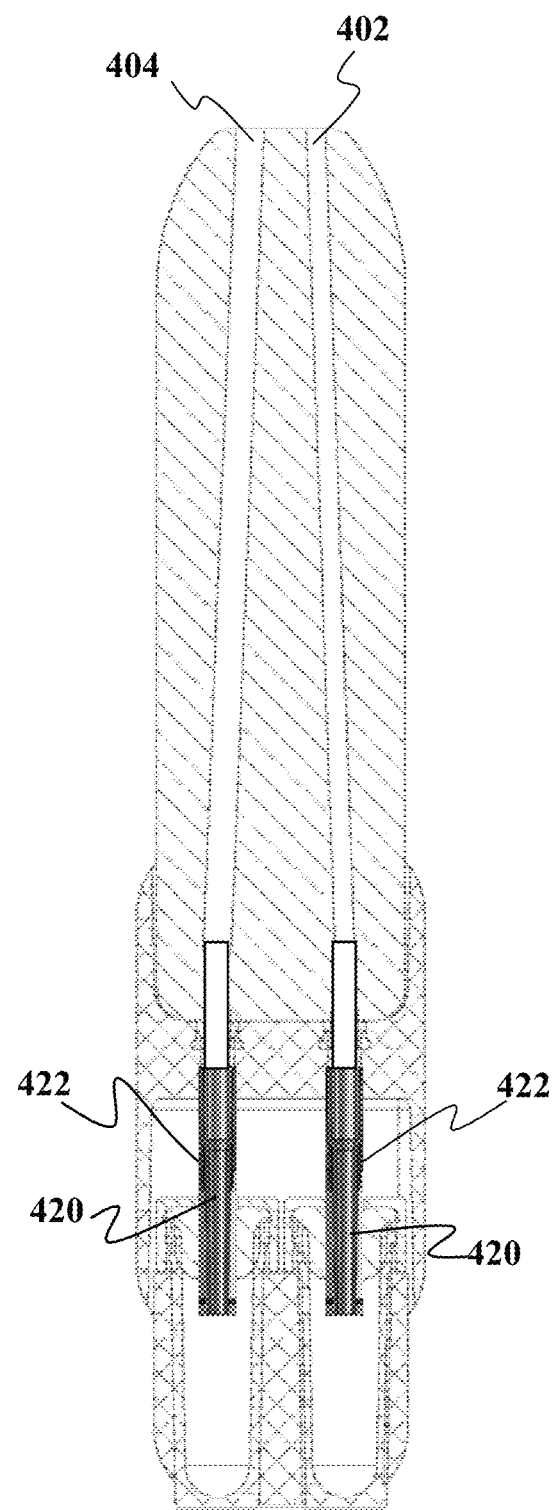
FIG. 42  FIG. 43

METHODS AND DEVICES FOR SAMPLE COLLECTION AND STABILIZATION

BACKGROUND

A blood sample for use in laboratory testing is often obtained by way of venipuncture, which typically involves inserting a hypodermic needle into a vein on the subject. Blood extracted by the hypodermic needle may be drawn directly into a syringe or into one or more sealed vials for subsequent processing. When a venipuncture may be difficult or impractical such as on a newborn infant, a non-venous puncture such as a heel stick or other alternate site puncture may be used to extract a blood sample for testing. After the blood sample is collected, the extracted sample is typically packaged and transferred to a processing center for analysis.

Unfortunately, conventional sample collection and testing techniques of bodily fluid samples have drawbacks. For instance, except for the most basic tests, blood tests that are currently available typically require a substantially high volume of blood to be extracted from the subject. Because of the high volume of blood, extraction of blood from alternate sample sites on a subject, which may be less painful and/or less invasive, are often disfavored as they do not yield the blood volumes needed for conventional testing methodologies. In some cases, patient apprehension associated with venipuncture may reduce patient compliance with testing protocol. Furthermore, the traditional collection technique may also waste sample be leaving portions behind the sample vessel.

INCORPORATION BY REFERENCE

All publications, patents, and patent applications mentioned in this specification are herein incorporated by reference to the same extent as if each individual publication, patent, or patent application was specifically and individually indicated to be incorporated by reference.

COPYRIGHT

This document contains material subject to copyright protection. The copyright owner (Applicant herein) has no objection to facsimile reproduction of the patent documents and disclosures, as they appear in the US Patent and Trademark Office patent file or records, but otherwise reserves all copyright rights whatsoever. The following notice shall apply: Copyright 2016 Theranos, Inc.

SUMMARY

At least some of disadvantages associated with the prior art are overcome by at least some or all of the embodiments described in this disclosure. Although the embodiments herein are typically described in the context of obtaining a blood sample, it should be understood that the embodiments herein are not limited to blood samples and can also be adapted to acquire non-blood body fluids, other fluid(s) or bodily sample(s) for analysis.

In one embodiment, a device is provided comprising at least one capillary tube; a nozzle located at a proximal end of the capillary tube; a least one collection vessel with a self-healing cap; wherein the vessel is configured to go from a vent, unvented, and then sealed configuration as the nozzle is removed from the vessel; wherein during nozzle removal when any venting of the vessel is sealed, continued pulling of the vessel provides for vacuum force to be created within the sample vessel, due in part of the pulling of the sealed vessel away from the device to draw out residual sample that may still be resident in the capillary tube; wherein the nozzle in this passive, gravity flow step has the nozzle in a vented state. Optionally, during removal, the nozzle enters into a non-vented state which then allows for creation of a vacuum in the target vessel which in turn pulls sample into the target vessel. In one embodiment, this suction effect is created by the nozzle forming a seal with the self-healing cap. Optionally, other embodiments may use other techniques to create this non-vented state.

In one embodiment, a method is provided comprising one pushing the vessel forward towards a distal end of the device to create relative motion that moves the nozzle through a self-healing cap of the vessel; a one-step motion is used to remove the sample vessel from the sample collection device; wherein the motion to remove the sample vessel also draws residual sample from the nozzle into the sample vessel.

Optionally, the device may comprise at least one pierceable cap on at least one of the sample vessel. This removes the capping step that is used in traditional devices. In this manner, the sample is never full exposed in an uncapped state to the atmosphere. This reduces potential for biological contamination. Optionally, no mixing step by the user is used to mix the anti-coagulant because in part: a) there is mixing when the residual sample is pulled into the sample vessel and/or b) coating in the capillary tube also provides anti-coagulant to the sample. It should be understood that a sufficient amount of anti-coagulant applied within a certain time window can stabilize the sample for subsequent processing. Optionally, in addition to the anti-coagulants, the amount of time that the sample is exposed in an uncapped state while the sample is in the vessel is also relevant to sample stabilization. Optionally, some embodiments may have a vented nozzle design to allow for capture of residual sample and this reduces sample loss. This removes the tapping step that technicians often use to mix or to move residual sample into the vessel. In embodiments, the ergonomic housing allows for greater dexterity during collection. In embodiments, the guide or other portion of the sample collection device automatically covers bloody tip after collection to reduce possible contamination.

In embodiments, the nozzle and plug reduces puncture force while providing greater contact area on plunger. In one embodiment, the plug comprises a thermoplastic elastomer. In embodiments, using the nozzles is safer and cheaper alternative to steel needles with pointed tips. In embodiments, using capillary tube/nozzle eliminates need for hard center plastic plug and associated assembly step for a needle based system. The absence of a hard plug allows for conical inner shape to reduce overage.

Optionally, some embodiments may use a motive force from the vessel after gravity flow drains sample from the capillary tube into the vessel to improve better collection or yield of sample into the vessel.

Optionally, the inner channel of the capillary tube is coated with at least one anti-coagulant. In one embodiment, the amount of EDTA is at least about 1.5 mg/ml. In one embodiment, the amount of EDTA is at least about 1.8 mg/ml. In one embodiment, the amount of EDTA is at least about 1.9 mg/ml. In one embodiment, the amount of EDTA is at least about 2 mg/ml. In one embodiment, the amount of EDTA in a coating of the channel is sufficient such that at least about 2 mg/ml enters the sample. Optionally, the inner channel of the capillary tube is coated with at least one anti-coagulant and the sample vessel. In at least one embodiment, the amount of EDTA in the channel and vessel is at least about 2 mg/ml. In at least one embodiment, the amount of EDTA in the channel and vessel is at least about 2.2 mg/ml. In one embodiment, the concentration of anti-coagulant in coating of the channel may be greater than the amount in the coating of the sample vessel. In one embodiment, the amount of EDTA in a coating of the channel and sample vessel is sufficient such that at least about 2 mg/ml enters the sample.

In embodiments, a sample vessel containing a small volume of bodily fluid sample may be transported. The sample and sample vessel may have any of the respective characteristics described elsewhere herein. In embodiments, a sample vessel may contain less than or equal to 5 ml, 3 ml, 4 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl bodily fluid sample. In embodiments, a sample vessel may have an interior volume of less than or equal to 5 ml, 3 ml, 4 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl. In embodiments, a sample vessel may have an interior volume of less than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl, and may contain bodily fluid sample which fills at least 10%, 20%, 30%, 40%, 50%, 60%, 70%, 80%, 90%, 95%, 98%, 99%, or 100% of the interior volume of the vessel. In embodiments, the sample vessel may be sealed, for example, with a cap, lid, or membrane. Any of the vessel interior dimensions or sample dimensions described herein may apply to the interior dimensions of a sealed sample vessel, or to the dimensions of a sample therein, respectively. In embodiments, a sealed sample vessel may have an interior volume of less than or equal to 5 ml, 4 ml, 3 ml, 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, or 5 µl, and it may contain bodily fluid sample which fills at least 10%, 20%, 30%, 40%, 50%, 60%, 70%, 80%, 90%, 95%, 98%, 99%, or 100% the interior volume of the vessel, such that less than or equal to 2 ml, 1.5 ml, 1 ml, 750 µl, 500 µl, 400 µl, 300 µl, 200 µl, 150 µl, 100 µl, 75 µl, 50 µl, 40 µl, 30 µl, 20 µl, 10 µl, 5 µl, 4 µl, 3 µl, 2 µl, or 1 µl of air is present in the interior volume of the sealed vessel. Thus, for example, a sealed sample vessel may have an interior volume of less than or equal to 300 µl and it may contain bodily fluid sample which fills at least 90% of the interior volume of the vessel, such that less than or equal to 30 ul of air is present in the interior volume of the sealed vessel. In another example, a sealed sample vessel may have an interior volume of less than or equal to 500 µl and it may contain bodily fluid sample which fills at least 80% of the interior volume of the vessel, such that less than or equal to 100 ul of air is present in the interior volume of the sealed vessel. In another example, a sealed sample vessel may have an interior volume of less than or equal to 150 µl and it may contain bodily fluid sample which fills at least 98% of the interior volume of the vessel, such that less than or equal to 3 µl of air is present in the interior volume of the sealed vessel.

In embodiments, sample vessels containing a sample may also contain an anticoagulant. The anticoagulant may be dissolved in the sample or otherwise present in the vessel (e.g. dried on one or more interior surfaces of the vessel or in solid form at the bottom of the vessel). A sample vessel containing a sample may have a "total anticoagulant content", wherein the total anticoagulant content is the total amount of anticoagulant present in the interior volume of the vessel, and includes anticoagulant dissolved in the sample (if any), as well as anticoagulant in the vessel which is not dissolved in the sample (if any). In one embodiment, the concentration of heparin in the sample vessel is in the range of about 10 to 30 US Pharmacopeia (USP) units heparin per 1 ml. In one embodiment, the concentration of EDTA in the sample vessel is in the range of about 1 to about 3 mg of EDTA per 1 ml.

In embodiments, a sample vessel containing a sample may contain no more than 1 ml sample and have a total anticoagulant content of no more than 3 mg EDTA but more than 1 mg of EDTA, may contain no more than 750 µl sample and have a total anticoagulant content of no more than 2.3 mg EDTA but more than 1 mg of EDTA, may contain no more than 500 µl sample and have a total anticoagulant content of no more than 1.5 mg EDTA but more than 1 mg of EDTA, may contain no more than 400 µl sample and have a total anticoagulant content of no more than 1.2 mg EDTA but more than 0.8 mg of EDTA, may contain no more than 300 µl sample and have a total anticoagulant content of no more than 0.9 mg EDTA but more than 0.5 mg of EDTA, may contain no more than 200 µl sample and have a total anticoagulant content of no more than 0.6 mg EDTA but more than 0.4 mg of EDTA, may contain no more than 150 µl sample and have a total anticoagulant content of no more than 0.45 mg EDTA but more than 0.3 mg of EDTA, may contain no more than 100 µl sample and have a total anticoagulant content of no more than 0.3 mg EDTA but more than 0.1 mg of EDTA, may contain no more than 75 µl sample and have a total anticoagulant content of no more than 0.23 mg EDTA but more than 0.07 mg of EDTA, may contain no more than 50 µl sample and have a total anticoagulant content of no more than 0.15 mg EDTA but more than 0.07 mg of EDTA, may contain no more than 40 µl sample and have a total anticoagulant content of no more than 0.12 mg EDTA but more than 0.06 mg of EDTA, may contain no more than 30 µl sample and have a total anticoagulant content of no more than 0.09 mg EDTA but more than 0.05 mg of EDTA, may contain no more than 20 µl sample and have a total anticoagulant content of no more than 0.06 mg EDTA but more than 0.03 mg of EDTA, may contain no more than 10 µl sample and have a total anticoagulant content of no more than 0.03 mg EDTA but more than 0.01 mg of EDTA, or may contain no more than 5 µl sample and have a total anticoagulant content of no more than 0.015 mg EDTA but more than 0.007 mg of EDTA. In embodiments, a sample vessel containing a sample may contain no more than 1 ml sample and have a total anticoagulant content of no more than 2 mg EDTA, may contain no more than 750 µl sample and have a total anticoagulant content of no more than 1.5 mg EDTA, may contain no more than 500 µl sample and have a total anticoagulant content of no more than 1 mg EDTA, may contain no more than 400 µl sample and have a total anticoagulant content of no more than 0.8 mg EDTA, may contain no more than 300 µl sample and have a total anticoagulant content of no more than 0.6 mg EDTA, may contain no more than 200 µl sample and have a total anticoagulant content of no more than 0.4 mg EDTA, may contain no more than 150 µl sample and have a total anticoagulant content of no more than 0.3 mg EDTA, may contain no more than 100 µl sample and have a total anticoagulant content of no more than 0.2 mg EDTA, may contain no more than 75 µl sample and have a total anticoagulant content of no more than 0.15 mg EDTA, may contain no more than 50 µl sample and have a total anticoagulant content of no more than 0.1 mg EDTA, may contain no more than 40 µl sample and have a total anticoagulant content of no more than 0.08 mg EDTA, may contain no more than 30 µl sample and have a total anticoagulant content of no more than 0.06 mg EDTA, may contain no more than 20 µl sample and have a total anticoagulant content of no more than 0.04 mg EDTA, may contain no more than 10 µl sample and have a total anticoagulant content of no more than 0.02 mg EDTA, or may contain no more than 5 µl sample and have a total anticoagulant content of no more than 0.01 mg EDTA. In embodiments, a sample vessel containing a sample may contain no more than 1 ml sample and have a total anticoagulant content of no more than 30 US Pharmacopeia (USP) units heparin, may contain no more than 750 µl sample and have a total anticoagulant content of no more than 23 USP units heparin, may contain no more than 500 µl sample and have a total anticoagulant content of no more than 15 USP units heparin, may contain no more than 400 µl sample and have a total anticoagulant content of no more than 12 USP units heparin, may contain no more than 300 µl sample and have a total anticoagulant content of no more than 9 USP units heparin, may contain no more than 200 µl sample and have a total anticoagulant content of no more than 6 USP units heparin, may contain no more than 150 µl sample and have a total anticoagulant content of no more than 4.5 USP units heparin, may contain no more than 100 µl sample and have a total anticoagulant content of no more than 3 USP units heparin, may contain no more than 75 µl sample and have a total anticoagulant content of no more than 2.3 USP units heparin, may contain no more than 50 µl sample and have a total anticoagulant content of no more than 1.5 USP units heparin, may contain no more than 40 µl sample and have a total anticoagulant content of no more than 1.2 USP units heparin, may contain no more than 30 µl sample and have a total anticoagulant content of no more than 0.9 USP units heparin, may contain no more than 20 µl sample and have a total anticoagulant content of no more than 0.6 USP units heparin, may contain no more than 10 µl sample and have a total anticoagulant content of no more than 0.3 USP units heparin, or may contain no more than 5 µl sample and have a total anticoagulant content of no more than 0.15 USP units heparin. In embodiments, a sample vessel containing a sample may contain no more than 1 ml sample and have a total anticoagulant content of no more than 15 USP units heparin, may contain no more than 750 µl sample and have a total anticoagulant content of no more than 11 USP units heparin, may contain no more than 500 µl sample and have a total anticoagulant content of no more than 7.5 USP units heparin, may contain no more than 400 µl sample and have a total anticoagulant content of no more than 6 USP units heparin, may contain no more than 300 µl sample and have a total anticoagulant content of no more than 4.5 USP units heparin, may contain no more than 200 µl sample and have a total anticoagulant content of no more than 3 USP units heparin, may contain no more than 150 µl sample and have a total anticoagulant content of no more than 2.3 USP units heparin, may contain no more than 100 µl sample and have a total anticoagulant content of no more than 1.5 USP units heparin, may contain no more than 75 µl sample and have a total anticoagulant content of no more than 1.2 USP units heparin, may contain no more than 50 µl sample and have a total anticoagulant content of no more than 0.75 USP units heparin, may contain no more than 40 µl sample and have a total anticoagulant content of no more than 0.6 USP units heparin, may contain no more than 30 µl sample and have a total anticoagulant content of no more than 0.45 USP units heparin, may contain no more than 20 µl sample and have a total anticoagulant content of no more than 0.3 USP units heparin, may contain no more than 10 µl sample and have a total anticoagulant content of no more than 0.15 USP units heparin, or may contain no more than 5 µl sample and have a total anticoagulant content of no more than 0.08 USP units heparin.

In embodiments, sample vessels may contain a blood clotting activator (e.g. thrombin, silica particles, glass particles), an antiglycolytic agent (e.g. sodium floride), or a gel to facilitate the separation of blood cells from plasma. In examples, sample vessels may contain sodium polyanethol sulfonate (SPS), acid citrate dextrose additives, perchloric acid, or sodium citrate. Some embodiments may include at least one material from each of the above groupings. Optionally, it should also be understood that other additives or materials are not excluded, particularly if the additives do not interfere with each other in terms of functionality.

Optionally, a sample collection device is provided that draws sample into the device by first motive force, which in one nonlimiting example, comprises capillary force. A second motive force, which in one nonlimiting example is gravity, is used to move at least some portion of the sample into the sample vessel. In this non-limiting example, a third motive force is used to move at least some portion of any sample remaining in a channel or tube leading to the sample vessel, which in this embodiment is a suction force created in the sample vessel. In this non-limiting example, the third motive force is a suction created when the nozzle is in a sealed interface with the outer diameter of the collection tube or channel while there is still relative motion between the sample vessel and the tube or channel. This relative motion while there is a sealed interface creates a negative pressure build-up inside the sample vessel which then causes at least some portion of the sample in the capillary tube to be "urged" into the sample vessel due to the negative pressure environment. This use of at least three different motive forces allows for improved collection of sample from the sample collection device. Optionally, some embodiments may use still other motive forces to draw any remaining sample into the device. Of course, due to the size scale of some of the collection tubes and vessels, it may be possible to use some conventional techniques, such as tapping on the device, to facilitate fluid transfer. In one embodiment, each of these at least three motive forces are each different from one another. Optionally, some embodiments may have three motive forces, wherein only two of the motive forces are different from one another.

Optionally, the inner diameter of the capillary is designed to allow collection and for gravity drain.

Optionally, this vessel collecting sample can also be design to work with a 9 mm pitch. Optionally, the vessel can be sized to fit in a pitch that is common and used in other laboratory equipment.

In embodiments, the slidable holder of the sample vessel will also pull out a portion of the way to guide the pulling out of the sample vessel to keep it centrally aligned as it pulls out. The slidable holder also helps close any vents along the nozzle and such closing of vents helps generate vacuum pulling force in the sample vessel to extract any sample left at the tip of the capillary tube. In embodiments, the slidable holder slides but does not detach from the sample collection device. In this manner, it can guide the sample vessel through part of the "stroke" to decouple the sample vessel from the sample collection device, although at some point, the guide stops sliding and remains attached to the sample collection device while the sample vessel, in at least some embodiments, continues to be movable until fully detached from the sample collection device.

Optionally, active drawing or pulling of the cap over of the nozzle while in a sealed interface creates a suction through the coaxial channel of the nozzle to draw remaining sample out of the capillary tube. It creates a non-vented state wherein continuing to pull on the nozzle creates a vacuum to help draw out any remaining sample in the collection channel, tube, or tip. This non-vented state assisted draw is useful for extracting those remaining drops that reside in the channel, tube, or tip. It does not require tapping of the sample vessel to extract the sample from the capillary tube, because such tapping is user dependent on executing that move.

In some embodiments, there may be anti-coagulant in both the capillary and in the vessel. The vessel anticoagulant may be a precipitate. In some embodiments, the anti-coagulant is evenly applied to walls of the vessel and/or capillary tube. In some embodiments, the capillary tubes comprise PET-G. Optionally, some embodiments may use glass capillary tubes. If the diameter is too large on the capillary, the collection tube may be sensitive to how much tilting occurs during collection. Optionally, the parts may be made of one of the following: PMMA, PET, PET-G, or similar material currently known or may be developed. Optionally, the parts may be made of at least one or more of the following: PMMA, PET, PET-G, or similar material currently known or may be developed.

In one embodiment, the channel can collect about 285 uL. Optionally, the channel collects 300 uL. Optionally, the channel collects no more than 300 uL but more than 20 uL. Optionally, the channel collects no more than 285 uL but more than 40 uL. Optionally, the channel collects no more than 250 uL but more than 40 uL. Optionally, the channel collects no more than 225 uL but more than 40 uL. Optionally, the channel collects no more than 200 uL but more than 40 uL. Optionally, the channel collects no more than 190 uL but more than 40 uL. Optionally, the channel collects no more than 180 uL but more than 40 uL. Optionally, the channel collects no more than 170 uL but more than 40 uL. Optionally, the channel collects no more than 160 uL but more than 40 uL. Optionally, the channel collects no more than 150 uL but more than 40 uL.

Optionally, some embodiments may "flare" a tip to increase diameter to assist in engaging larger sample "beads" or pools. Capillary tube sticks out from the end by an amount such as but not limited to 1/16 of an inch.

Optionally, in the vessel, after sample fill, the head space to sample ratio is no more than about 0.2 to 1. Optionally, in the vessel, after sample fill, the head space to sample ratio is no more than about 0.3 to 1. Optionally, in the vessel, after sample fill, the head space to sample ratio is no more than about 0.4 to 1. Optionally, in the vessel, after sample fill, the head space to sample ratio is between about 0.2:1 to 0.3:1. Optionally, in the vessel, after sample fill, the head space to sample ratio is between about 0.1:1 to 0.2:1.

Optionally, in one embodiment, a pen portion of the housing comprises a guide 240 of the housing 260 that is used to guide the vessel sliding in and out of the device.

By using a capillary tube and other features of the embodiments therein, this can reduce clotting, reduce hemolysis, improve ease of use, improve lab automation, and/or improve manufacturability.

In one embodiment, the capping and upcapping can also be improved by the silicone cap which may be used for cap 230, which can be pressed on in sheets. In embodiments, it is pre-pierced (but self-sealing). There is not be enough of a gap to vent during this pre-piercing.

If one coats the sample vessel interior walls with anti-coagulant, in at least some embodiments, it is also desirable to coat the capillary tube with anti-coagulant so that both are coated and able to treat the sample.

It should be understood that the plug, when provided in groups, may make the device more laboratory automation friendly during manufacture and/or processing as the plug that can be put on and removed in bulk (such as but not limited 96 at a time). Optionally, the pierceable cap may not be ventable. If press-fit, then it might be an embodiment where it can vent. Optionally, one can have a special shaped tip that can allow for venting. To avoid a droplet that may drop onto the cap from tip, suction effect can reduce contamination and sample loss.

Optionally, the channel in the nozzle may have a draft to it to allow for manufacturability. It does taper for some draft that it slows the flow a bit. Optionally, the nozzle is press-fit over the end of the capillary tube, although other attachment techniques are not excluded. If outer diameter of nozzle is larger, then one gets more suction when pulling during the non-vented state. In some embodiments, the outer diameter of nozzle can only handle so much stretching. In embodi-ments, the self-healing cap will stay open and cannot fully self-recover if left punctured for an extended period of time.

Optionally, there may be a dual channel or dual tube embodiment wherein the vessel has at least two nozzles. There may be some way to route the blood into two separate tubes. In embodiment using the nozzle, there are also no "needles" to puncture a vessel, which may sometimes pierce a user or technician. Optionally, the use of pre-formed tubes also simplifies manufacturing as there is less need for expensive equipment such as but not limited to ultrasonic welding equipment to join parts together.

It should be understood that at least some or all of the sample collection device comprises a transparent material to allow for visualization of the collected sample in the capil-lary channel or capillary tube therein. This allows the technician to better perceive the fill state of the device. Optionally, the entire device is substantially transparent. Optionally, at least a majority of the device is substantially transparent. Optionally, only portions necessary to visualize sample being captured and/or stored in the device is trans-parent.

In embodiments, provided herein is a device comprising: a channel comprising an anticoagulant coating; and a vessel configured to be in fluid communication with the channel, wherein the device is configured to: receive, in the channel, a bodily fluid sample provided by a subject; mix, in the channel, the bodily fluid sample with the anticoagulant coating to generate a mixed bodily fluid sample based on a fluid flow of at least a portion of the bodily fluid sample across the anticoagulant coating; and collect, in the vessel, the mixed bodily fluid sample, wherein the anticoagulant coating comprises EDTA, and wherein the mixed bodily fluid sample comprises a bulk concentration of EDTA no less than about 2.5 milligrams per milliliter and no greater than about 10 milligrams per milliliter. In embodiments, the bulk concentration of EDTA is no less than about 3 milli-grams per milliliter and no greater than about 4 milligrams per milliliter. In embodiments, the device is further config-ured to mix the bodily fluid sample with the anticoagulant without generating a local concentration of EDTA greater than about 10, 15, 20, 25, 30, 35, 40, 45, or 50 milligrams per milliliter. In embodiments, the device is further config-ured to mix the bodily fluid sample with the anticoagulant with a shear rate no greater than about 1,000 reciprocal seconds. In embodiments, the channel of the device comprises a hydraulic diameter no less than about 0.5 millimeters and no greater than about 10 millimeters. In embodiments, the channel of the device comprises a mixing element, and wherein the device is further configured to mix, in the channel, the bodily fluid sample with the anticoagulant coating based on an advection. In embodiments, a concentration of the anticoagulant coating varies along a length of the channel according to a gradient. In embodiments, a magnitude of the gradient of the anticoagulant concentration decreases as the distance from an open end of the channel increases. In embodiments, a thickness of the anticoagulant coating varies along a length of the channel according to a gradient. In embodiments, a magnitude of the gradient of the anticoagulant thickness decreases as the distance from an open end of the channel increases. It should be understood that in some embodiments, the channel is defined by a tube. Optionally, in some embodiments, the channel is defined by a body that is not tube shaped. Optionally, some embodiments may use at least two pieces fused or otherwise joined together to define the channel therein.

In embodiments provided herein comprising a mixing element in a channel, the mixing element may comprise a protrusion on a surface of the channel. Optionally, the mixing element may comprise a staggered herringbone structure on a surface of the channel.

In embodiments, a bodily fluid sample prepared in a device, system, or method as provided herein may contain a concentration of EDTA of at least 0.1, 0.5, 1, 1.5, 2, 2.5, 3, 3.5, 4, 4.5, 5, 6, 7, 8, 9, or 10 mg EDTA/ml, of no more than 0.5, 1, 1.5, 2, 2.5, 3, 3.5, 4, 4.5, 5, 6, 7, 8, 9, 10, 15, or 20 mg EDTA/ml, or of at least 0.1, 0.5, 1, 1.5, 2, 2.5, 3, 3.5, 4, 4.5, 5, 6, 7, 8, 9, or 10 mg EDTA/ml and no more than 0.5, 1, 1.5, 2, 2.5, 3, 3.5, 4, 4.5, 5, 6, 7, 8, 9, 10, 15, or 20 mg EDTA/ml.

In embodiments, provided herein is a device comprising: a channel comprising an anticoagulant coating; and a vessel configured to be in fluid communication with the channel, wherein the device is configured to: receive, in the channel, a bodily fluid sample provided by a subject; mix, in the channel, the bodily fluid sample with the anticoagulant coating to generate a mixed bodily fluid sample based on a fluid flow of at least a portion of the bodily fluid sample across the anticoagulant coating; and collect, in the vessel, the mixed bodily fluid sample, wherein the anticoagulant coating comprises heparin, and wherein the mixed bodily fluid sample comprises a bulk concentration of heparin no less than about 20 units per milliliter and no greater than about 150 units per milliliter. In embodiments, the bulk concentration of heparin is no less than about 30 units per milliliter and no greater than about 50 units per milliliter. In embodiments, the device is further configured to mix the bodily fluid sample with the anticoagulant with a shear rate no greater than about 1,000 reciprocal seconds. In embodiments, the channel comprises a hydraulic diameter no less than about 0.5 millimeters and no greater than about 10 millimeters. In embodiments, the channel comprises a mixing element, and the device is further configured to mix, in the channel, the bodily fluid sample with the anticoagulant coating based on an advection. In embodiments, a concentration of the anticoagulant coating varies along a length of the channel according to a gradient. In embodiments, a magnitude of the gradient of the anticoagulant concentration decreases as the distance from an open end of the channel increases. In embodiments, a thickness of the anticoagulant coating varies along a length of the channel according to a gradient. In embodiments, a magnitude of the gradient of the anticoagulant thickness decreases as the distance from an open end of the channel increases.

In embodiments, a bodily fluid sample prepared in a device, system, or method as provided herein may contain a concentration of heparin of at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, or 250 units heparin/ml, of no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, 250, 300, 350, 400, or 500 units heparin/ml, or at least 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, or 250 units heparin/ml and no more than 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 110, 120, 130, 140, 150, 200, 250, 300, 350, 400, or 500 units heparin/ml.

In embodiments, provided herein is a method comprising: receiving, in a channel, a bodily fluid sample provided by a subject; mixing the bodily fluid sample with an anticoagulant to generate a mixed bodily fluid sample; and collecting, in a vessel in fluid communication with the channel, the mixed bodily fluid sample, wherein the anticoagulant comprises EDTA, and wherein the mixed bodily fluid sample comprises a bulk concentration of EDTA no less than about 2.5 milligrams per milliliter and no greater than about 10 milligrams per milliliter. In embodiments, mixing the bodily fluid sample with the anticoagulant comprises mixing the bodily fluid sample with the anticoagulant without generating a local concentration of EDTA greater than about 20 milligrams per milliliter. In embodiments, the mixed bodily fluid sample reaches the bulk concentration of EDTA at a time less than 90 seconds after the bodily fluid sample was initially received in the channel. In embodiments, mixing the bodily fluid sample with the anticoagulant comprises mixing the bodily fluid sample with the anticoagulant with a shear rate no greater than about 1,000 reciprocal seconds.

In embodiments, a bodily fluid sample prepared in a device, system, or method as provided herein may reach a stated concentration of an anticoagulant (e.g. EDTA or heparin) within no more than 5, 10, 15, 20, 25, 30, 40, 50, 60, 70, 80, 90, 100, 110, 120, 130, 140, 150, 180, or 210 seconds after the bodily fluid sample is initially released from a subject's body. In embodiments, a bodily fluid sample prepared in a device, system, or method as provided herein may reach a stated concentration of an anticoagulant (e.g. EDTA or heparin) within no more than 5, 10, 15, 20, 25, 30, 40, 50, 60, 70, 80, 90, 100, 110, 120, 130, 140, 150, 180, or 210 seconds after the skin of a subject's body is pierced (e.g. with a lancet or needle) to release the bodily fluid sample.

In embodiments, provided herein is a method comprising: receiving, in a channel, a bodily fluid sample provided by a subject; mixing the bodily fluid sample with an anticoagulant to generate a mixed bodily fluid sample; and collecting, in a vessel in fluid communication with the channel, the mixed bodily fluid sample, wherein the anticoagulant comprises heparin, and wherein the mixed bodily fluid sample comprises a bulk concentration of heparin no less than about 20 units per milliliter and no greater than about 150 units per milliliter. In embodiments, the mixed bodily fluid sample reaches the bulk concentration of heparin at a time less than 90 seconds after the bodily fluid sample was initially received in the channel. In embodiments, mixing the bodily fluid sample with the anticoagulant comprises mixing the bodily fluid sample with the anticoagulant with a shear rate no greater than about 1,000 reciprocal seconds.

In at least one embodiment, the anti-coagulant level in the capillary tube is at least 2 mg/ml. At least one embodiment has anti-coagulant in both the capillary tube and in the vessel that collects the sample. At least one embodiment has anti-coagulant in both the capillary tube and in the vessel that collects the sample, wherein the anti-coagulant level in the capillary tube is at least 2 mg/ml. At least one embodiment has anti-coagulant in both the capillary tube and in the vessel that collects the sample, wherein the anti-coagulant level in the capillary tube and in the vessel is at least 2 mg/ml.

In one embodiment described herein, a device is provided comprising at least one sample collection channel and at least one collection vessel, wherein the vessel is configured to go from a vent, unvented, and then sealed configuration as the vessel is moved along a path to disengage from the sample collection channel.

In another embodiment described herein, a method is provided comprising: providing a sample collection device comprising at least one sample collection channel and at least one collection vessel coupled to receive sample from the collection channel, wherein the vessel is configured to go from a vent, unvented, and then sealed configuration as the vessel is moved along a path to disengage from the sample collection channel. In one embodiment, the technique from removing the sample vessel from the sample collection channel comprising motion along a linear pathway. Optionally, the method comprises moving the sample vessel along a non-linear pathway. Optionally, the method of removing the sample vessel occurs in a single continuous motion until the sample vessel is no longer in fluid communication with the sample collection channel. Optionally, the condition of the sample vessel from vented to unvented condition does not involve using a valve or active mechanism in the cap of the sample vessel. Optionally, in one embodiment, only static components are used to the condition of the sample vessel from vented to unvented condition during motion of the sample vessel. Optionally, in another embodiment, there may be an active component such as a valve in either the sample vessel or cap of the sample vessel this is changed in state (vent versus unvented) depending on where the sample vessel or cap is located along the sample collection channel. For example, there may be one or more features such as but not limited to protrusion on an outer surface of the collection channel that when the cap of the sample vessel slides over the protrusion, it closes a vent in the cap and creates an unvented condition. Optionally, there may be one or more features such as but not limited to protrusion on an outer surface of the collection channel that when the cap of the sample vessel slides over the protrusion, it opens a vent in the cap and creates a vented condition. Optionally, the active mechanism may be in the sample collection channel and one or more features such as but not limited to protrusion on an outer surface of the sample collection vessel or the cap triggers action in the mechanism. Optionally, for any of the embodiments herein, instead of a mechanical feature to trigger actuation of the mechanism, an electronic tag or other marker can be used to trigger actuation in a mechanism in the sample vessel, the cap of the sample vessel, the sample channel, or any single or multiple combination (or all) of the foregoing. This may include but it not limited to a bar code, optical marker, RFID, magnetic, or other non-mechanical trigger.

Optionally, the condition of the sample vessel from vented to unvented condition depends on where the cap is located along the sample collection channel and structure(s) associated with the sample collection channel. Optionally, the condition of the sample vessel from vented to unvented condition depends on where the cap is located along the sample collection channel and structure(s) associated with the sample collection channel which can act as a vent when the cap of the vessel is engaged or over certain sections of the sample collection channel.

Optionally, a method is provided comprising at least one technical feature from any of the prior features. Optionally, the method comprises at least any two technical features from any of the prior features. Optionally, a device is provided comprising at least one technical feature from any of the prior features. Optionally, the device comprises at least any two technical features from any of the prior features. Optionally, the system is provided comprising at least one technical feature from any of the prior features. Optionally, the system comprises at least any two technical features from any of the prior features.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIGS. 42 and 43 show cross-sectional views of another embodiment of a sample collection device as described herein.

DETAILED DESCRIPTION

Figure 1:
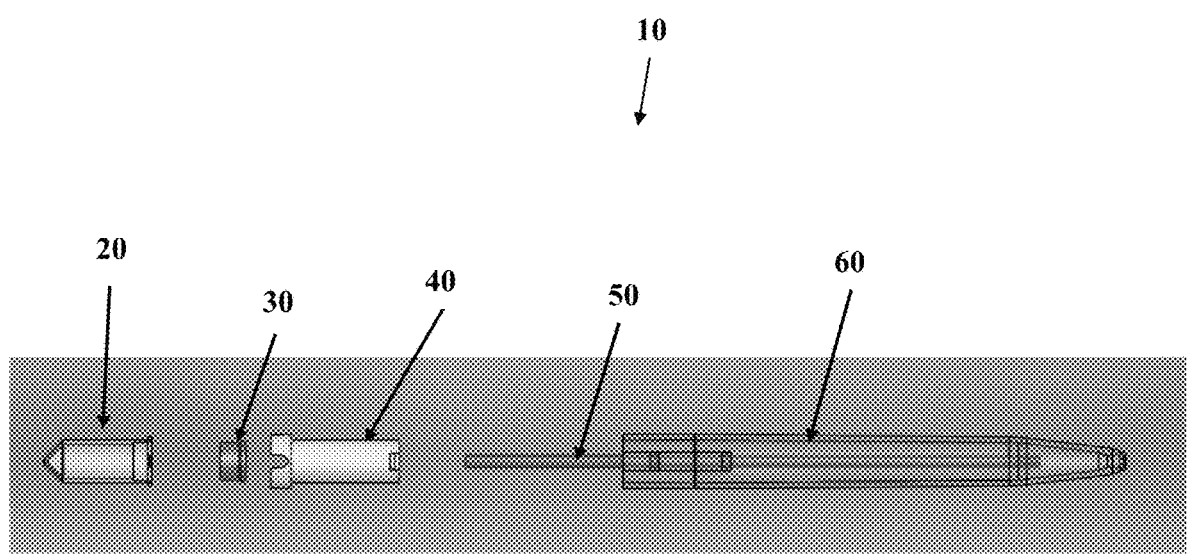
FIG. 1 shows an exploded side view of one embodiment of a device described herein.

It is to be understood that both the foregoing general description and the following detailed description are exemplary and explanatory only and are not restrictive of the invention, as claimed. It may be noted that, as used in the specification and the appended claims, the singular forms "a", "an" and "the" include plural referents unless the context clearly dictates otherwise. Thus, for example, reference to "a material" may include mixtures of materials, reference to "a compound" may include multiple compounds, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for a sample collection unit, this means that the sample collection unit may or may not be present, and, thus, the description includes both structures wherein a device possesses the sample collection unit and structures wherein sample collection unit is not present.

As used herein, the terms "substantial" means more than a minimal or insignificant amount; and "substantially" means more than a minimally or insignificantly. Thus, for example, the phrase "substantially different", as used herein, denotes a sufficiently high degree of difference between two numeric values such that one of skill in the art would consider the difference between the two values to be of statistical significance within the context of the characteristic measured by said values. Thus, the difference between two values that are substantially different from each other is typically greater than about 10%, and may be greater than about 20%, preferably greater than about 30%, preferably greater than about 40%, preferably greater than about 50% as a function of the reference value or comparator value.

As used herein, a "sample" may be but is not limited to a blood sample, or a portion of a blood sample, may be of any suitable size or volume, and is preferably of small size or volume. In some embodiments of the assays and methods disclosed herein, measurements may be made using a small volume blood sample, or no more than a small volume portion of a blood sample, where a small volume comprises no more than about 5 mL; or comprises no more than about 3 mL; or comprises no more than about 2 mL; or comprises no more than about 1 mL; or comprises no more than about 500 µL; or comprises no more than about 250 µL; or comprises no more than about 100 µL; or comprises no more than about 75 µL; or comprises no more than about 50 µL; or comprises no more than about 35 µL; or comprises no more than about 25 µL; or comprises no more than about 20 µL; or comprises no more than about 15 µL; or comprises no more than about 10 µL; or comprises no more than about 8 µL; or comprises no more than about 6 µL; or comprises no more than about 5 µL; or comprises no more than about 4 µL; or comprises no more than about 3 µL; or comprises no more than about 2 µL; or comprises no more than about 1 µL; or comprises no more than about 0.8 µL; or comprises no more than about 0.5 µL; or comprises no more than about 0.3 µL; or comprises no more than about 0.2 µL; or comprises no more than about 0.1 µL; or comprises no more than about 0.05 µL; or comprises no more than about 0.01 µL.

As used herein, the term "point of service location" may include locations where a subject may receive a service (e.g. testing, monitoring, treatment, diagnosis, guidance, sample collection, ID verification, medical services, non-medical services, etc.), and may include, without limitation, a subject's home, a subject's business, the location of a healthcare provider (e.g., doctor), hospitals, emergency rooms, operating rooms, clinics, health care professionals' offices, laboratories, retailers [e.g. pharmacies (e.g., retail pharmacy, clinical pharmacy, hospital pharmacy), drugstores, supermarkets, grocers, etc.], transportation vehicles (e.g. car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, bodily fluid sample acquisition sites (e.g. blood collection centers), sites at or near an entrance to a location that a subject may wish to access, sites on or near a device that a subject may wish to access (e.g., the location of a computer if the subject wishes to access the computer), a location where a sample processing device receives a sample, or any other point of service location described elsewhere herein.

In embodiments, the device comprises a capillary tube with a nozzle pre-fit into one end of the tube. To prepare the device for collection, one pushes the vessel forward towards a distal end of the device which in turn moves the nozzle through a self-healing cap of the vessel. This "primes" the device. This may be beneficial in embodiments where leaving the tube in a fixed position inside the self-healing cap will prevent the cap from fully resealing.

In embodiments, the collection is performed through capillary force pulling sample into the capillary tube. Optionally, the entire capillary is tube is filled with sample. Optionally, some embodiments may be configured to draw sample a certain amount in the collection tube and not fill it entirely. Some embodiments may use optical markers, windows, or other visual methods to show when a sufficient amount of sample has been collected. Optionally, some embodiments may configure the capillary tube such as but not limited to venting, tube diameter size, tube cross-sectional shape, or other physical change to denote when filling is sufficient or even using such feature to stop capillary collection.

In embodiments, to move sample into the sample vessel, gravity is used. The collection device oriented vertically so that the sample flows out of the tube into the sample vessel based on the diameter of the capillary tube selected to allow such gravity pulling to overcome any capillary holding force of the capillary tube. The sample vessel is sufficiently vented to allow for sample to easily enter the sample vessel.

In embodiments, to remove the sample vessel from the collection device, a one-step motion is used to pull the sample vessel off of the sample collection device. As the pulling occurs, any venting of the interior of the vessel is sealed which also provides for vacuum force to be created within the sample vessel, due in part of the pulling of the vessel away from the device creating a suction effect. This vacuum force can help draw out any portion of residual sample that may still be resident in the capillary tube. This gravity based flow may be views in embodiments as a passive step to drain sample into the sample vessel. The nozzle in this passive, gravity flow step has the nozzle in a vented state. During the pull, the nozzle enters into a non-vented state which then allows for creation of a vacuum in the target vessel which in turn pulls sample into the target vessel. In one embodiment, this suction effect is created by the nozzle forming a seal with the self-healing cap. Optionally, other embodiments may use other techniques to create this non-vented state.

Referring now to FIG. 1, an exploded side-view of one embodiment of the sample collection device 10 will now be described. FIG. 1 shows a vessel 20, a pre-slit plug 30 configured to engage the vessel 20, a vessel guide 40, a capillary tube 50, and a housing 60 that may have an elongate, pen-like shape. As seen in FIG. 1, the vessel 20 and pre-slit plug 30 may engage at least a portion of the vessel guide 40 so that the vessel 20 and pre-slit plug 30 may move in and out of the housing along a controlled pathway. Although a co-axial style vessel guide 40 is used herein to guide the path of the vessel 20, it should be understood that other embodiments may use other types of guides such as guide rails, guide channel, guide pole, or other features to provide a controlled pathway in and out of the housing 60. Although the capillary tube 50 is shown as a discrete item, separate from the housing 60, it should be understood that some embodiments may have these items integrally formed. Although the plug 30 is shown as discrete from the vessel 20, it should be understood that some embodiments may have these items integrally formed. Although the embodiment in FIG. 1 and other embodiments illustrated herein are typically shown to be used with a single vessel 20, it should be understood that other embodiments may utilize more than one vessel 20 that can be coupled to a single capillary tube 50 or have multiple capillary tubes 50 to accommodate separate vessels. By way of non-limiting example, one embodiment may have a Y-splitter to send sample from a single inlet to multiple outlets.

Figure 2:
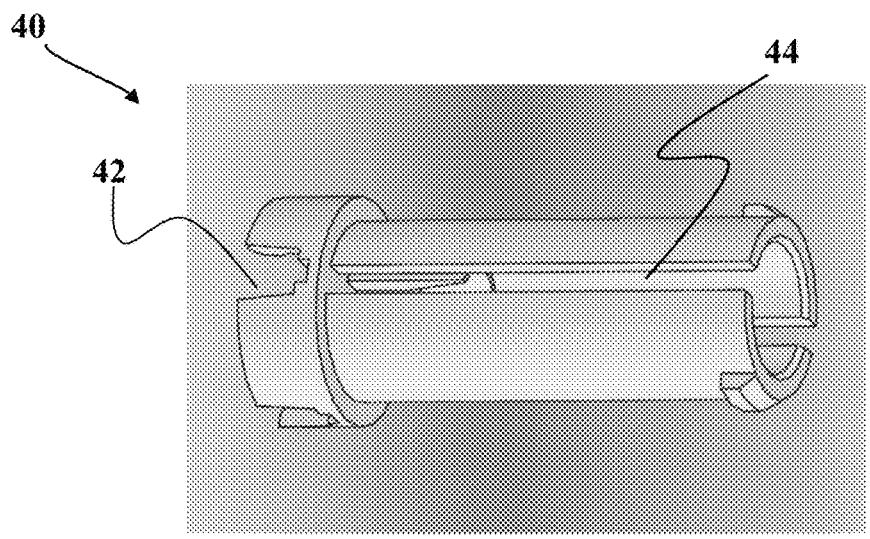
FIGS. 2 to 7 show various perspective views of components associated with the embodiment described in FIG. 1.

As seen in FIG. 2, one embodiment of the vessel guide 40 will now be described. In this embodiment, the vessel guide 40 includes a cap end 42 for engaging the vessel 20 and plug 30. By way of non-limiting example, the plug 30 may be a self-healing TPE plug as described herein. A guide channel 44 may be included along an elongate portion of the vessel guide 40. In one non-limiting example, this guide channel 44 is used to assist the orientation and path of the vessel guide 40 as portions of the vessel guide 40 slides inward and outward of the housing 60.

Figure 3:
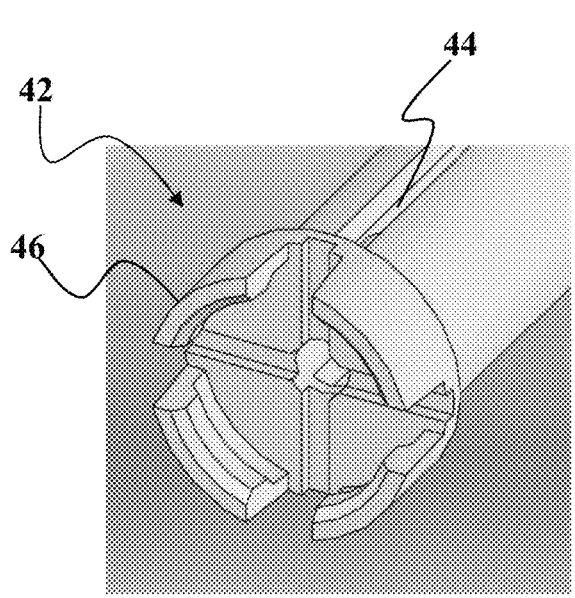

Referring now to FIG. 3, a perspective view of the cap end 42 is shown to illustrate one embodiment of grip structures 46 to engage the vessel 20 and/or plug 30. It should be understood that in some embodiments the grip structures 46 are bendable to allow for engagement and disengagement of the structures 46 from the sample vessel(s).

Figure 4:
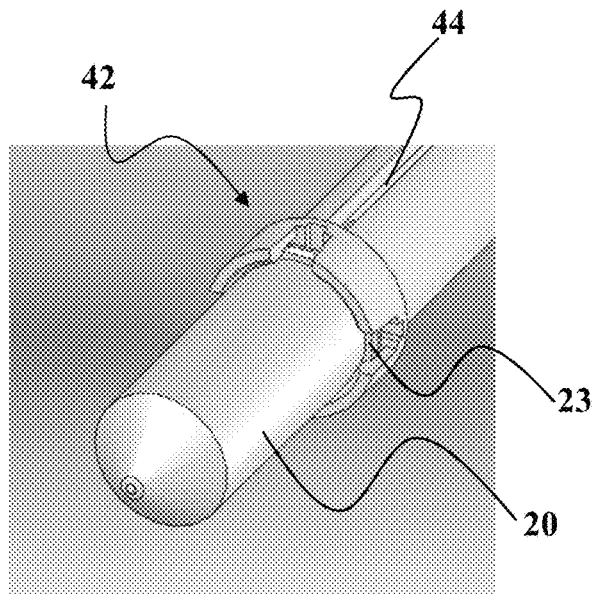

FIG. 4 shows another perspective view showing how the vessel 20 can be coupled to this particular embodiment of vessel guide 40. As seen in FIG. 4, the vessel 20 may include a lip 23 to engage at least a portion of the structures 26. Optionally, it should be understood that the reverse may also be used, wherein there is a lip structure on the vessel guide 40 and grip structure on the vessel 20.

Figure 5:
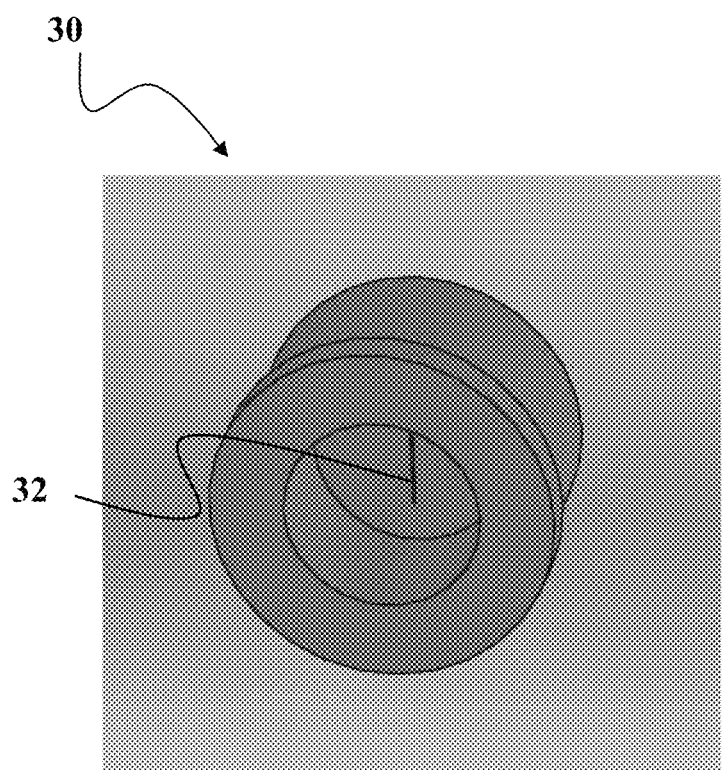

Referring now to FIG. 5, one embodiment of plug 30 will now be described. In this particular embodiment, it should be understood that the plug 30 includes a slit 32. Optionally, other embodiments may be configured without the slit, and are instead, self-healing material that can be pierced and reseal once the piercing element is removed. Optionally, some embodiments may be a material this is not-slit, but prior to use, is punctured at least once to create a pre-used path that will self-heal once the piercing member is removed, but the result is that the plug 30 will also be easier to penetrate on the next use due to the pre-use scenario.

Figure 6:
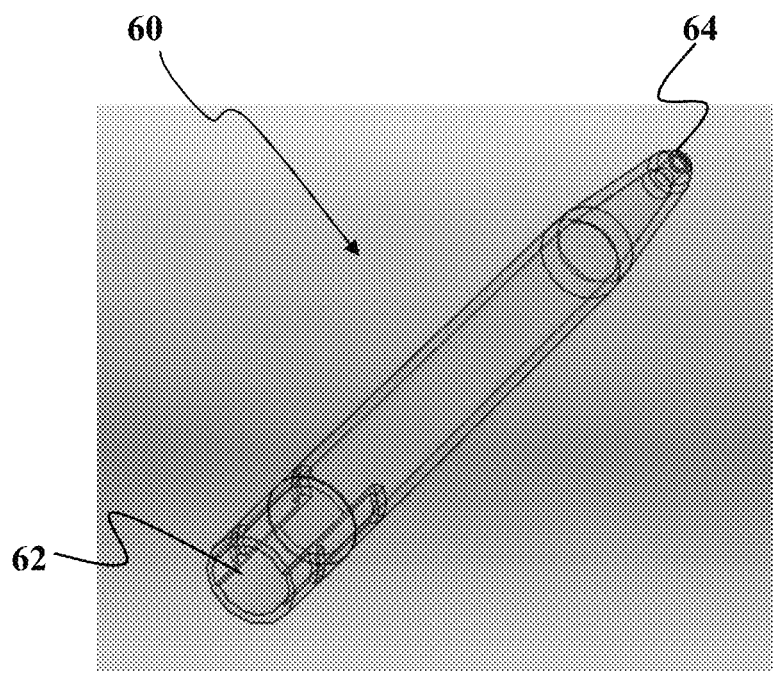
Figure 7:
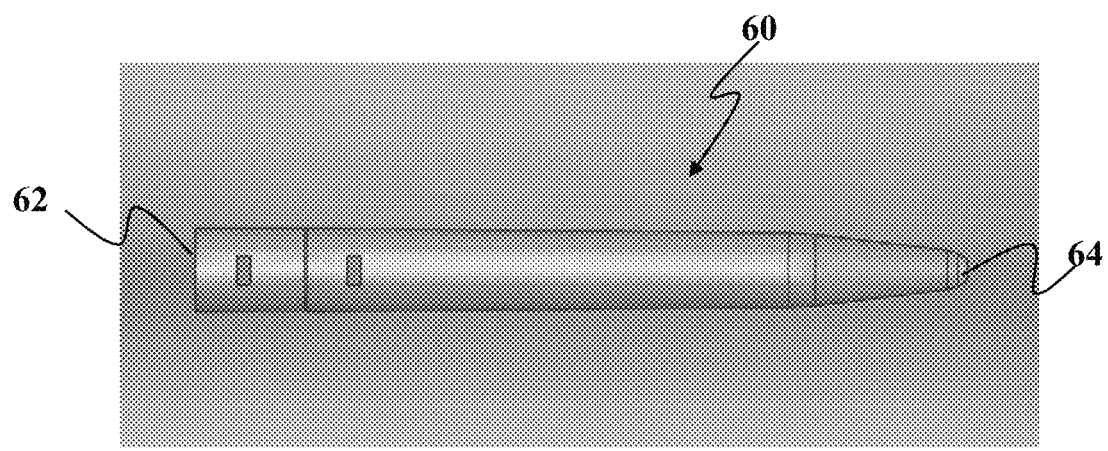

Referring now to FIGS. 6 and 7, embodiments of the housing 60 will now be described. As seen in the perspective view of FIG. 6, the housing 60 has a proximal opening 62 greater in lateral size than a distal opening 64. The housing 60 in this particular embodiment has an elongate, pen-shaped configuration.

Referring now to FIG. 7, a side view of the housing 60 is shown. It should be understood that in one embodiment, a capillary tube 50 is configured to be held inside the housing 60. Optionally, in other embodiments, the capillary tube 50 may be integrally formed with the housing 60. Optionally, instead of the tube 50 having a circular cross-sectional shape, it may have a cross-sectional shape selected from one or more of the following: square, rectangular, polygonal, oval, triangular, or single or multiple combinations of the foregoing. It should also be understood that in some embodiments, the cross-sectional shape is the same along the entire length of the tube or in some situations channel. Optionally, cross-sectional shape is different at different portions of the tube or in some situations channel.

Figure 8:
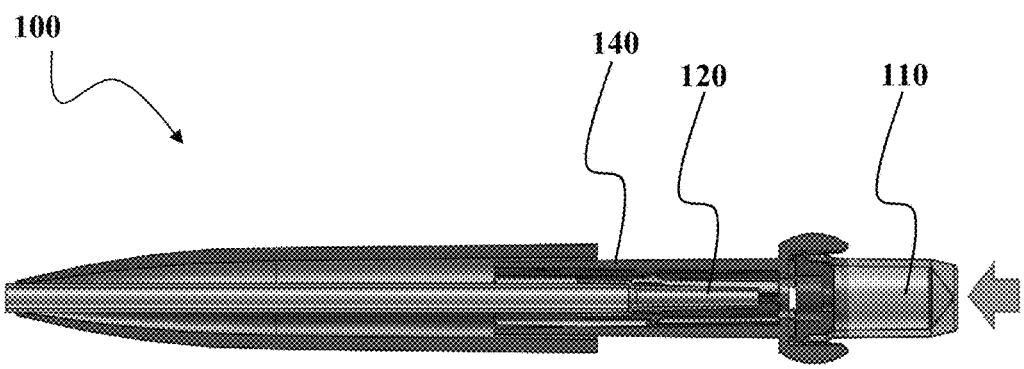
FIGS. 8 to 14 show various side views of another embodiment of a device as described herein.
Figure 9:
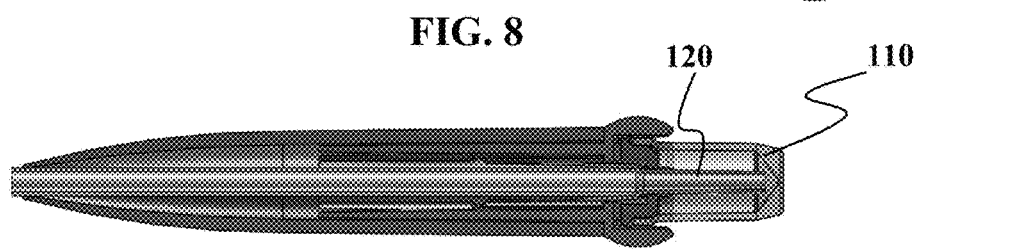
Figure 10:
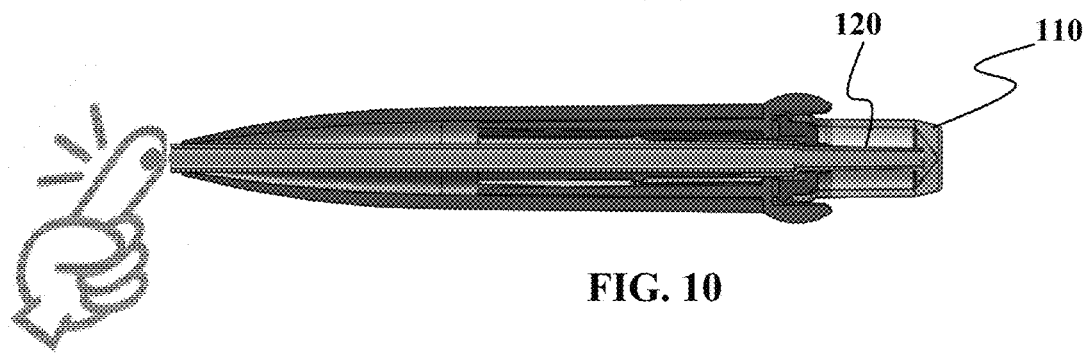

Referring now to FIGS. 8 to 10, a still further embodiment of a sample collection device 100 will now be described. FIG. 8 shows the sample collection device 100 in a normal state, wherein the sample vessel 110 has not been positioned to be in fluid communication with nozzle 120. In this non-limiting example, a guide 140 is used to assist in setting the pathway for the movement of the sample vessel 110. It should be understood that although the nozzle 120 and the capillary tube 150 are shown as separate pieces, it should be understood that in some embodiments, the nozzle 120 and the capillary 150 may be integrally formed. In some embodiments, the integration of the pieces may result in a simpler device because some of the interface components such as the receptor portion of the nozzle for coupling to the capillary tube may be eliminated. Optionally, some embodiments may use a capillary tube without the tapered inner channel of the nozzle 120, but instead use a straight inner channel without tapering of the inner channel. Optionally, other embodiments may increase the inner diameter of the channel.

FIG. 9 shows that the sample vessel 110 and the nozzle 120 are in fluid communication and where sample collected by device 100 can be deposited into the sample vessel 110. Although not limited in this manner, the nozzle 120 extends down to be near the bottom of the vessel 110. In one embodiment, the nozzle 120 is in the "tapered" bottom region of the sample vessel 110 when the sample vessel is ready to receive sample.

As seen in FIG. 10, sample which in this case is capillary blood from a finger, is collected into the capillary tube 150. In one embodiment, it is desirable to continue collecting sample into the capillary tube 150 until the entire tube is filled. By filling the entire tube, a known of amount of sample can be collection. Optionally, there may be other marks or indicators along the capillary tube 150 if a less-than-full tube collection is desired but having the marks allows for some indication to the operator or technician of the amount collected.

Figure 11:
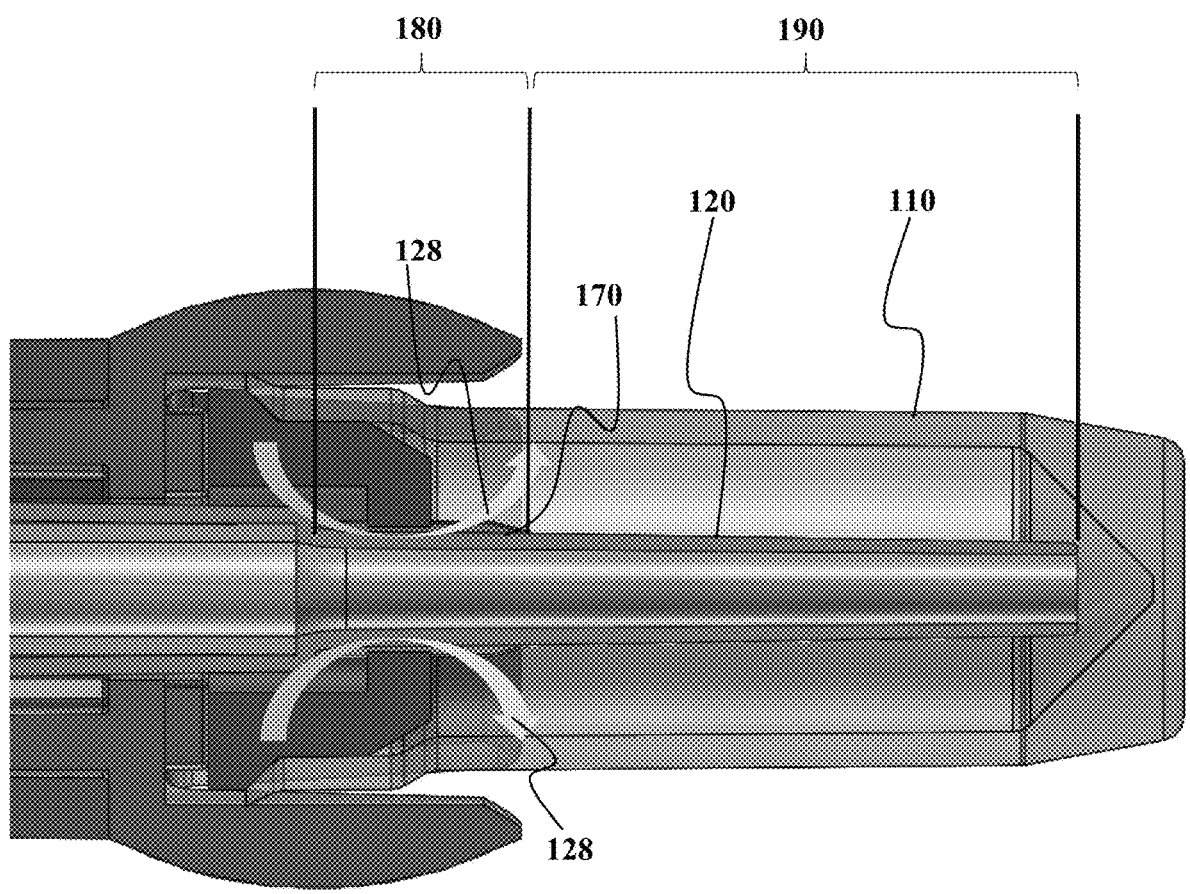

Referring now to FIG. 11, a close-up cross-sectional view of one embodiment of the vessel 110 and nozzle 120 will now be described. As seen in FIG. 11, the nozzle 120 has at least one portion at allows for a vented interface with the plug 130, while the nozzle 120 has at least another portion that is configured for a sealed, non-vented interface with the plug 130. It should be understood that in one embodiment, the vented interface is created through the use of surface structures 170 such as but not limited to ribs, bumps, or other indentations to create an imperfect seal with the plug 130 over zone 180. The venting allows for air flow in and out of the sample vessel 120 as shown by arrows 128.

Referring to still to FIG. 11, the seal along the nozzle 120 is formed in one embodiment by have a smooth surface on the nozzle 120 so that a non-vented interface is formed with the plug 130 over zone 190.

By having a vented and non-vented configuration, the sample collection device is configured so that the device may use at least three different motive forces at various points during the collection process to move the sample from the patient into the device and then into the sample vessel. By way of non-limiting example, the sample is first collected into the sample collection device 110 by a first motive force, which in the current embodiment is a capillary collection force to draw sample into the capillary tube. A second motive force, which in this embodiment is gravity, is used to move at least some portion of the sample into the sample vessel 110 when the sample collection device 100 is placed in vertical or other non-horizontal orientation to allow for a force such as gravity or simulated-gravity to move the sample into the sample vessel 110. In this non-limiting example, a third motive force is used to move at least some portion of any sample remaining in the capillary tube into the sample vessel 110, which in this embodiment is a suction force created when the nozzle 120 is in a sealed interface with the plug 130 while there is still relative motion between the sample vessel 110 and the nozzle 120. This relative motion while there is a sealed interface creates a negative pressure build-up inside the sample vessel 110 which then causes at least some portion of the sample in the capillary tube to be "urged" into the sample vessel 110 due to the negative pressure environment.

This use of at least three different motive forces allows for improved collection of sample from the sample collection device 100. Optionally, some embodiments may use still other motive forces to draw any remaining sample into the device. Of course, due to the size scale of some of the collection tubes and vessels, it may be possible to use some conventional techniques, such as tapping on the device, to facilitate fluid transfer.

As seen in FIG. 11, a proximal end of the nozzle 120 can be positioned close to the bottom of the vessel 110. Optionally, some may have the end of nozzle 120 in contact with at least some portion of the bottom of the sample vessel 110.

Figure 12:
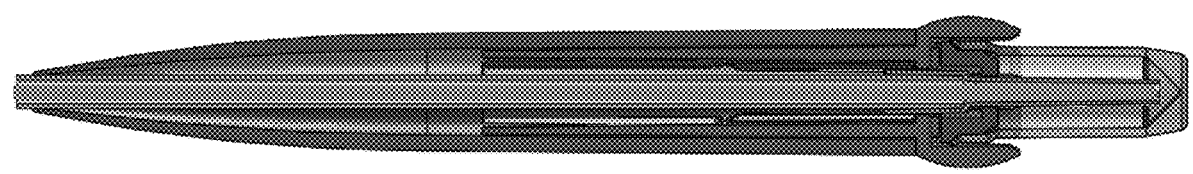
Figure 13:
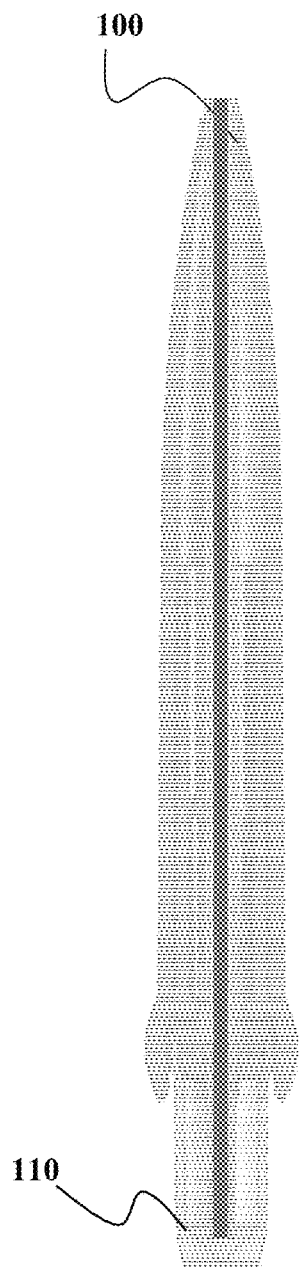
Figure 14:
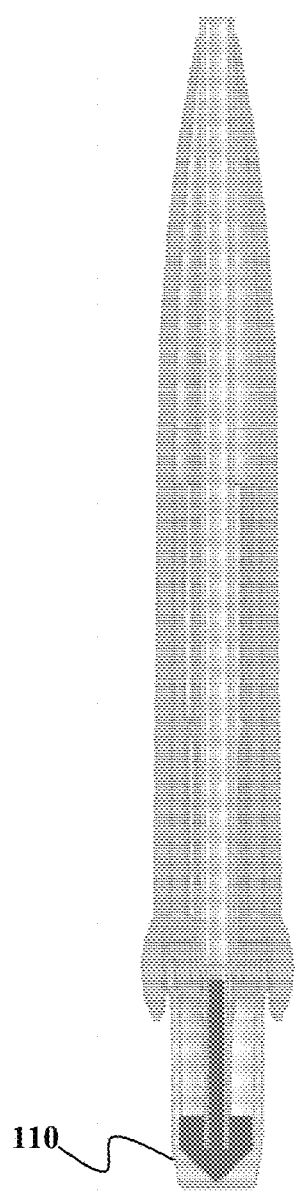

Referring now to FIGS. 12 to 14, one technique for transferring sample from the capillary tube 150 to the sample vessel 110 is shown. FIG. 12 shows that sample has filled the entire length of the capillary tube 150.

FIG. 13 shows the sample collection device 100 oriented in a non-horizontal position to allow gravity or similar force to overcome capillarity of the capillary tube 150 and assist the flow of sample out of the capillary tube 150 and into the sample vessel 110.

FIG. 14 shows that gravity will assist the flow of at least a portion of the sample into the sample vessel 110. It shows that, in at least some embodiments, at least some portion of the sample remains in the capillary tube 150, even when the sample collection device 110 is in the vertical orientation.

Some embodiments may use an additional force to further extract the remaining sample in the capillary tube 150 into the sample vessel 110. In one non-limiting example, further force such as provided by way of centrifugation can further assist the movement of sample into the sample vessel 110. In such a centrifugation scenario, the device 100 can be mounted to a cavity of the centrifuge with the sample vessel at the bottom of the cavity and then spinning the entire device on the centrifuge. Optionally, more than one sample collection device 100 can be mounted on the centrifuge for sample extraction.

Optionally, some embodiments may use a pressure differential to "push" the sample out of the capillary tube 150 and into the sample vessel 110. This "push" can be created by use of pressurized gas, a syringe, bulb, or other pressure source to assist movement of the sample. Optionally, a still further device may use a thin plunger to push sample out of the tube and into the sample container.

Figures 15, 16, 17, 18:
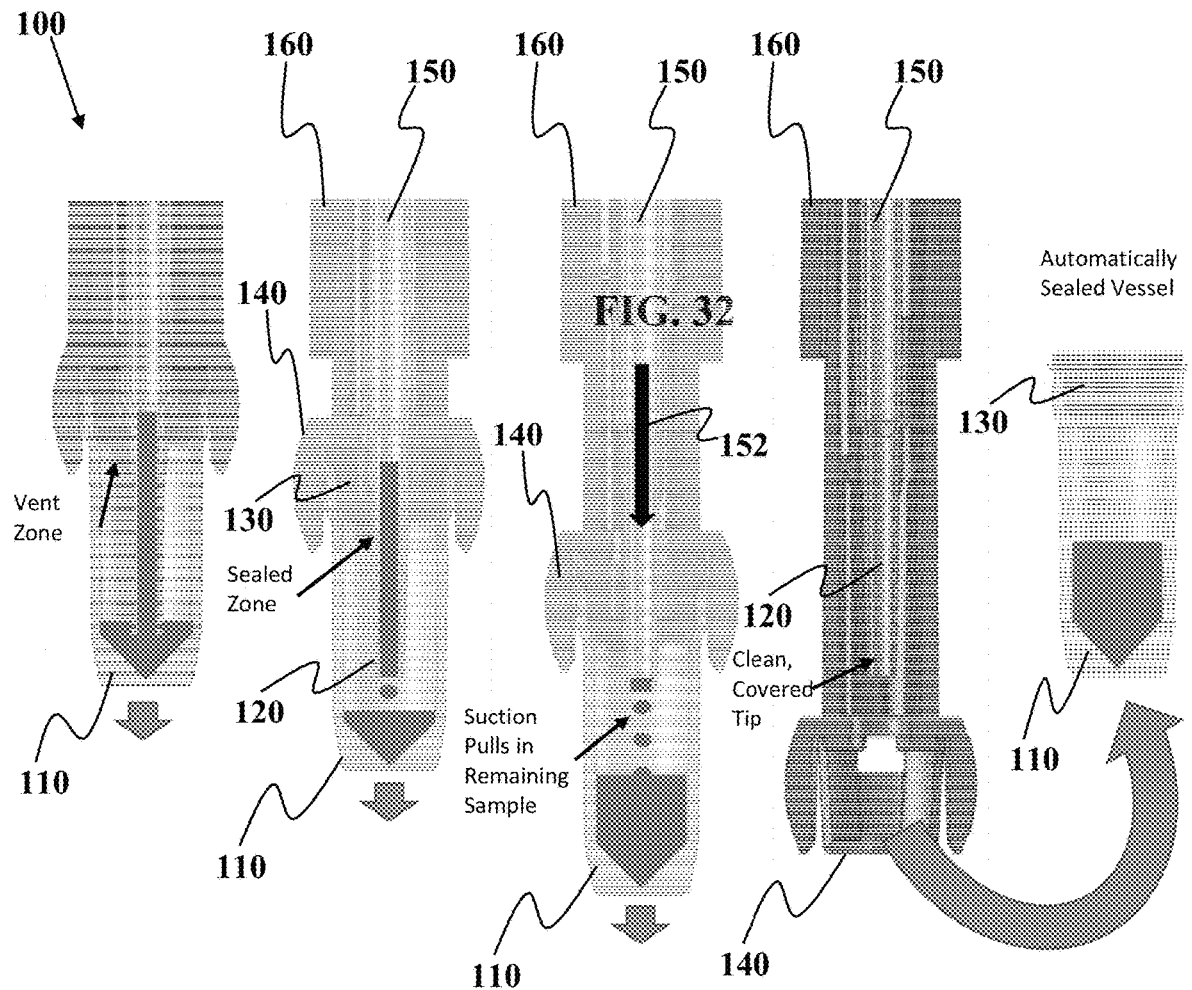
FIGS. 15 to 18 show one non-limiting example of a sequence of steps associated with detaching a sample vessel from one embodiment of a sample collection device.

Referring now to FIGS. 15 to 18, one embodiment of how sample is moved into the sample vessel 110 will now be described. As seen in FIG. 15, even after the device 100 is moved to a vertical orientation to allow gravity or similar force to "drain" sample into the sample vessel 110, at least some portion of the sample remains in the capillary tube 150 and/or the nozzle 120.

As seen in FIG. 16, relative motion of the guide 140 to the housing 160 starts to extend the guide 140 in a direction outward from the housing 160. FIG. 16 shows that in the present, non-limiting embodiment, the capillary tube 150 and nozzle 120 are in fixed relation to the housing 160, but the capillary tube 150 and nozzle 120 are slidable relation to the guide 140, sample vessel 110, and plug 130. As relative motion moves the guide 140 outward from the housing 160, relative motion is also created between the plug 130 and the nozzle 120. The relative motion between the plug 130 and the nozzle 130 transitions the interface between the plug 130 and nozzle 120 from a vented state due to at least one "imperfect" seal at the interface to a non-vented stated due to the sealed, non-vented condition of the interface between plug 130 and nozzle 120. In the present embodiment, the vent condition at the interface of the plug 130 and nozzle 120 also controls the vent state of the sample vessel 110. Accordingly, as the vent state changes at the interface between the plug 130 and the nozzle 120, so does the vent state of the sample vessel 110.

Referring now to FIG. 17, continued relative motion between the guide 140 and the housing 160 will increase the suction created inside the chamber of the sample vessel 110. This increased suction due to the non-vented state of the nozzle 120 and the plug 130 and motion of the sample vessel 110, will draw more sample into the sample vessel. This may be due in part the pushing force of air trying to enter the sample vessel 110 through the capillary tube 150 as indicated by arrow 152.

As seen in FIG. 18, once the guide 140 has been fully extended and/or the nozzle 120 has disengaged from the plug 130, the sample 110 can be decoupled from the guide 140 and separated from the sample collection device 110. In this non-limiting example, the plug 130 is formed of a self-healing material the reseals the pathway through the plug 130 used by the nozzle 120 to access the interior of the sample vessel 110. In this manner, the plug 130 if made of a self-healing material, will create and automatically sealed vessel once the sample vessel 110 is disconnected from the nozzle 120. This minimizes the amount of time, if any, that the sample is exposed to an atmosphere external the chamber of the sample vessel 110.

FIG. 18 shows the sample vessel 110 with plug 130 can be fully decoupled from the sample collection device 110 so that the smaller size of the sample vessel 110 is easier to transport in a shipping container or for processing equipment manipulate/handle.

It should be understood that although this embodiment uses the nozzle 120 to create the vented/non-vented state of the sample vessel 110, other techniques are not excluded. For example, other embodiments may only have portions of the nozzle 120 configured to form an imperfect seal, instead of having the imperfect seal extend around the entire circumference of the nozzle. Optionally, another vent pathway can be configured to extend through the plug 130 in a manner that allows the vent to be opened or closed as desired. For example, the vented/unvented state can be controlled by a finger covering a vent opening. Covering the vent opening creates a non-vented state in the sample vessel 110, which when coupled with relative motion of the sample vessel to the housing/capillary tube, can force residual sample in the capillary tube into the sample vessel 110. Of course, in place of a finger, other apparatus such as a cover, flap, housing portion, or other mechanism for opening and/or closing at least one vent.

Figure 19:
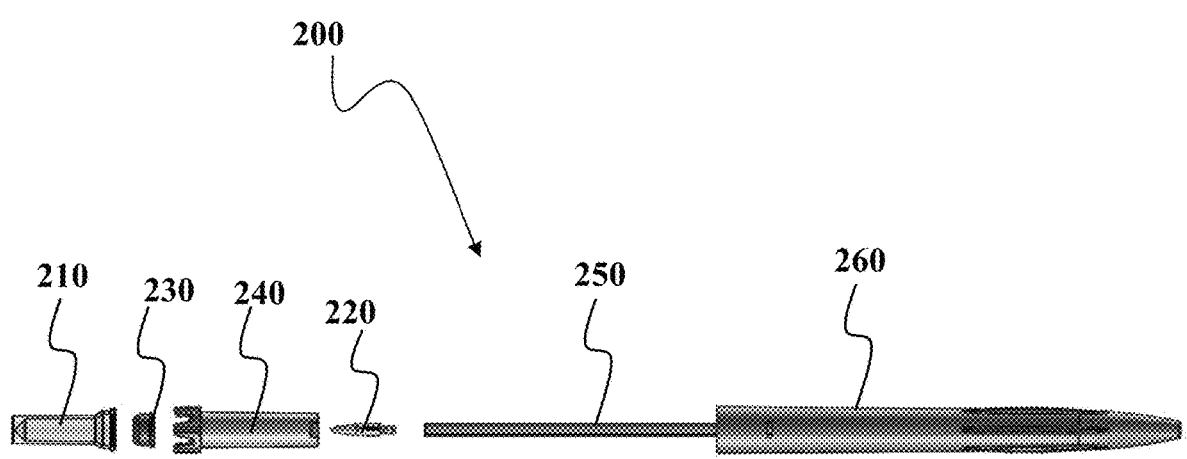
FIGS. 19 to 20 show views of embodiments of a device described herein.

Referring now to FIG. 19, a still further embodiment of a sample collection device 200 will now be described. FIG. 19 shows an exploded view of this embodiment of sample collection device 200. FIG. 19 shows a sample vessel 210 for use with a plug 230 that can be configured to engage a guide 240. In this present embodiment, a nozzle 220 is sized to engage the capillary tube 250 that is coupled to the housing 260. It should be understood that the nozzle 220 can be configured to have structure(s) along at least a portion of the nozzle 220 to allow for imperfect seal against the plug 230, while at least another portion of the nozzle 220 provides for a non-venting seal with the plug 230.

Figure 20:
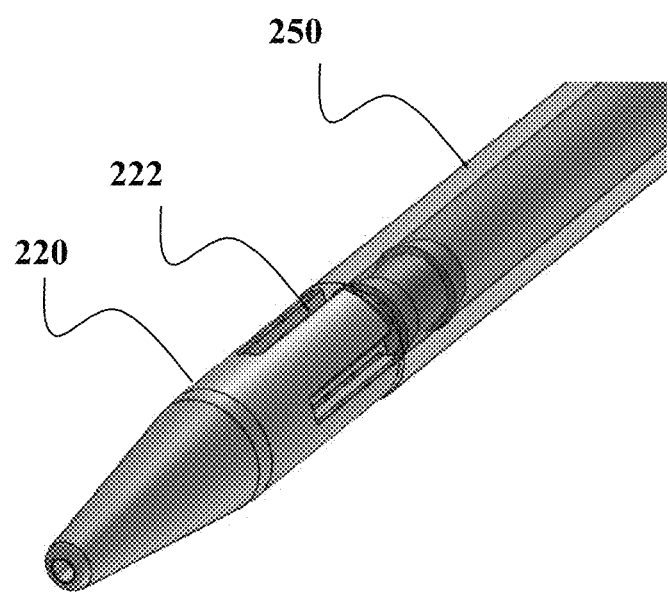

FIG. 20 provides a close-up perspective view of the nozzle 220 coupled to the capillary tube 250. As seen in FIG. 20, the nozzle 220 may include at least one structure 222 that allows for a vented condition when the plug 230 is engaged with the nozzle 220. In FIG. 20, the structure is a channel, groove, or similar structure that allows for a vented interface between nozzle 220 and the plug 230. Variable inside geometry allows for control of flow through capillary.

In embodiments, the vessel can be removed from outer housing with reduced risk of contamination and without need for tapping by technician. This is due in part because of the self-healing plug and in part because residual sample in the capillary tube 250 is urged into the sample vessel 210 based on vented/unvented states of the sample vessel 210. It should also be understood that in some capillary tube sizes, the tapping by the technician may be insufficient or inferior to using the technique herein of urging residual sample into the sample vessel 210.

Figure 21:
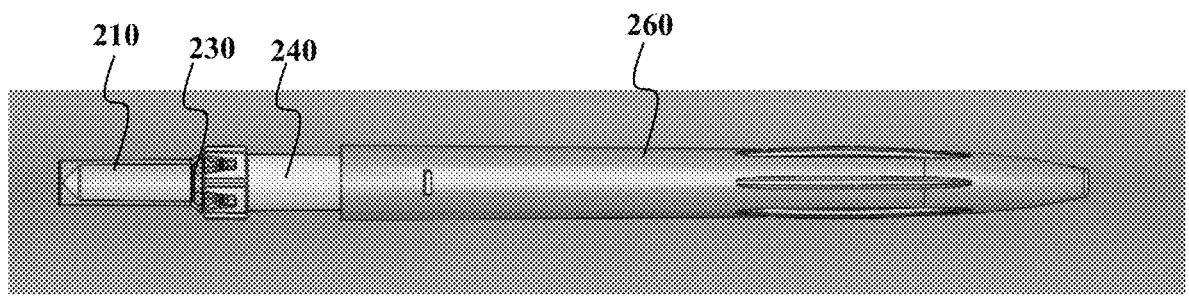
FIGS. 21 to 24 show various views of another embodiment of a device as described herein.

Referring now to FIGS. 21 to 24, the use of the sample collection device 200 will now be described. FIG. 21 shows the sample collection 200 in a resting, unprimed state, prior to use. As seen in FIG. 21, the guide 240 is in an outward extended position relative to the housing 260. This non-primed position is useful so that the nozzle 220 (not shown) is not engaged against the self-healing plug 230, wherein continued-extended contact with the nozzle 220 could deform the plug 230 to an extent that it cannot self-heal after the nozzle 220 is removed.

Figure 22:
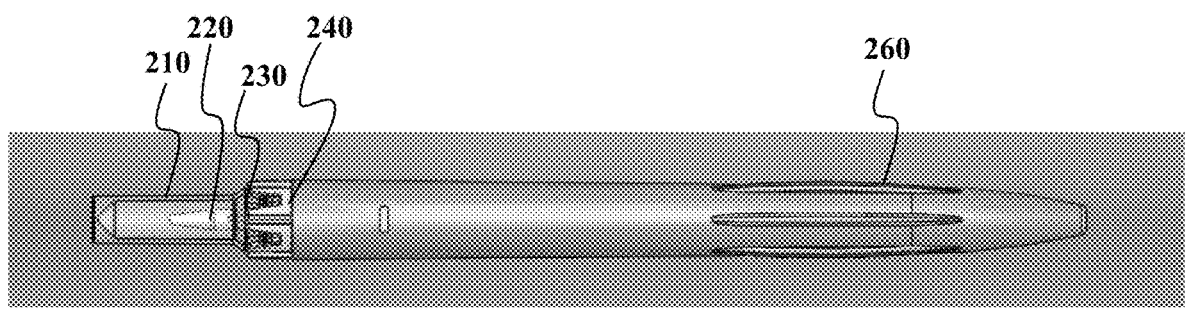

FIG. 22 shows that sample collection device 200 in a "ready for collection" state wherein the sample collection device 200 is primed. In the primed position, the nozzle 220 penetrates the plug 230.

Figure 23:
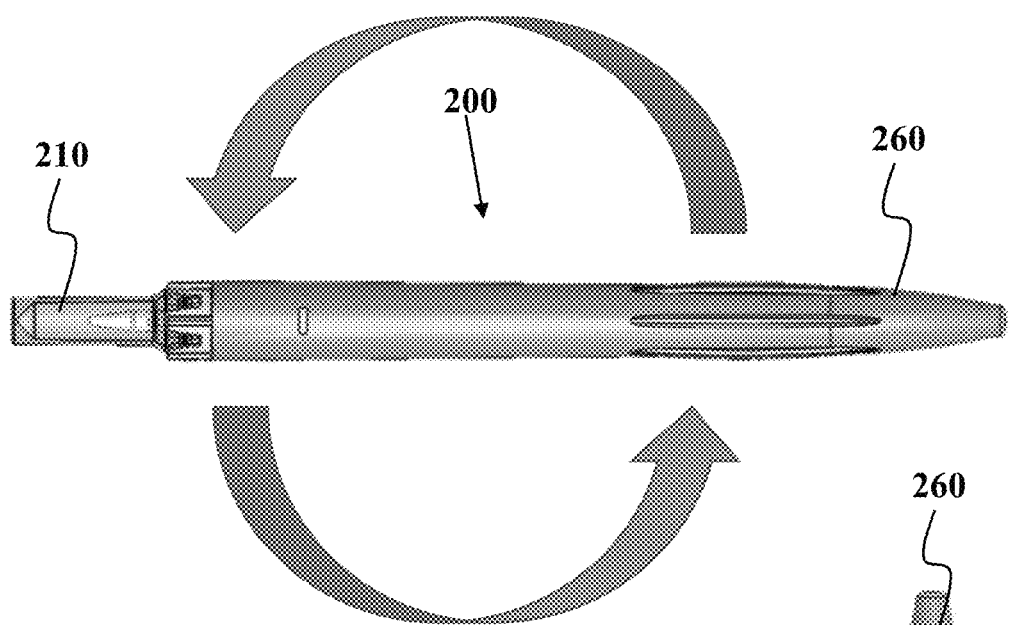

FIG. 23 shows that after sample is collected, the entire device 200 and be positioned in a non-horizontal manner to allow for gravity assisted flow of sample into the sample vessel 210.

Figure 24:
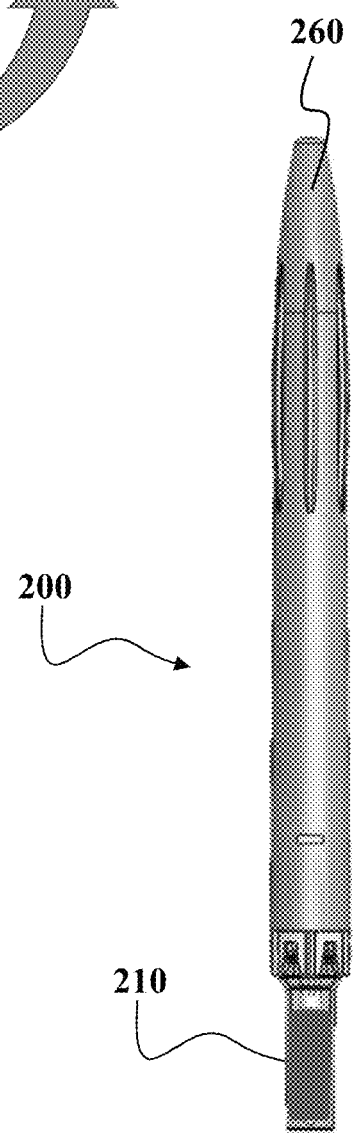

FIG. 24 shows the vessel in a vertical orientation. This vertical orientation maximizes the ability for gravity to assist flow into the sample vessel 210.

Figures 25, 26, 27:
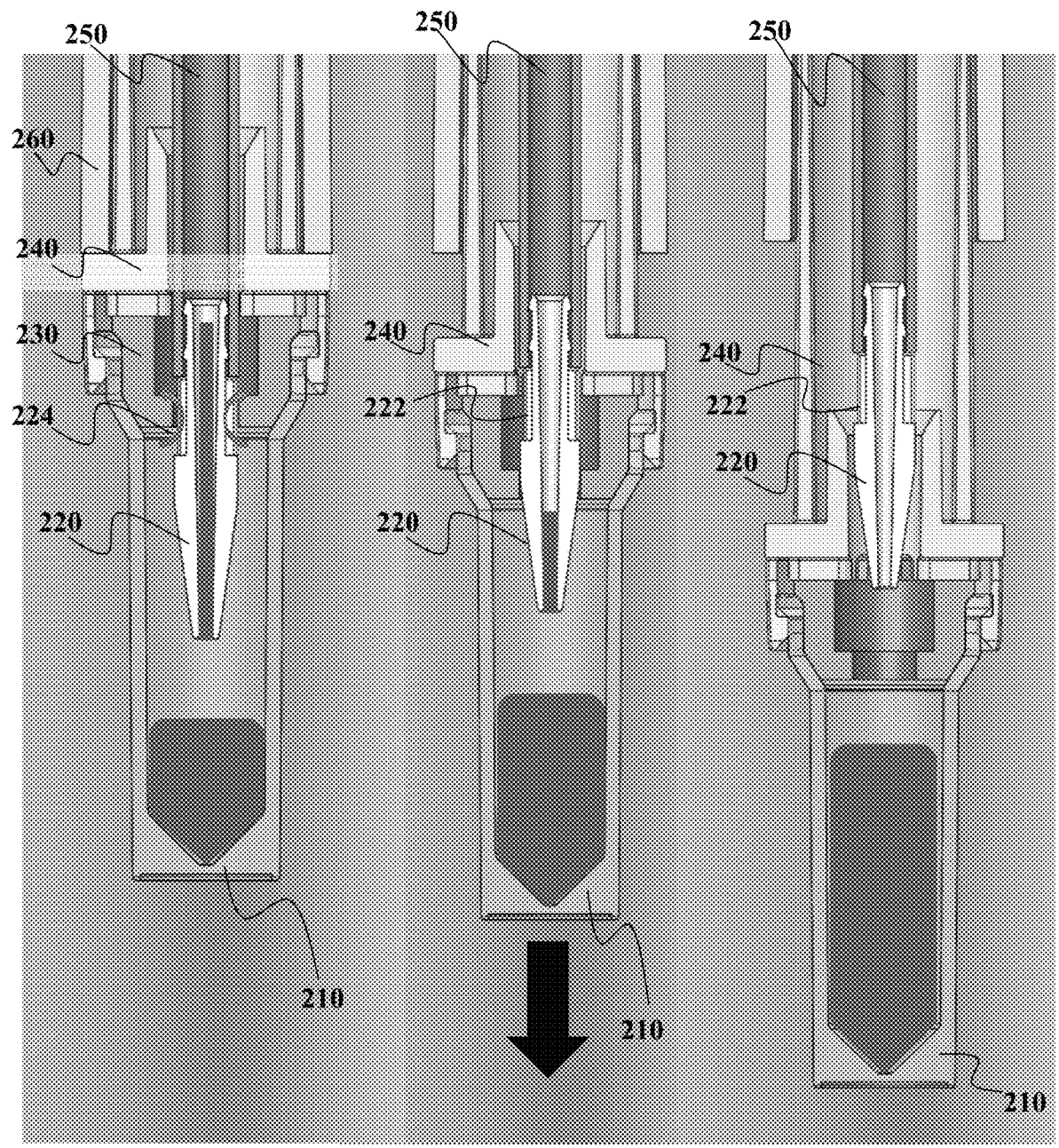
FIGS. 25 to 27 show one non-limiting example of a sequence of steps associated with detaching a sample vessel from one embodiment of a sample collection device.

Referring now to FIGS. 25 to 27, the process of using vented and unvented states of sample vessel 210 will now be described. FIG. 25 shows that there remains a portion of the sample in the nozzle 220. The nozzle 220 in FIG. 25 allows for venting through the plug 230 as indicated by arrows 224.

FIG. 26 shows that at least some portion of the guide 240 has begun to be extended away from the housing 260 and the capillary tube 250. This move changes the interface between the nozzle 220 and the plug 230, creating a sealed, non-venting interface with the plug 230. Moving the interface into a non-venting condition will urge any remaining sample in the capillary tube 250 and/or nozzle 220, due in part to the continued movement of the sample vessel away from the housing 260 that creates a "suction" effect to draw sample into the vessel.

FIG. 27 shows the sample vessel 210 extended away from the sample collection device 200 and the guide 240 in an extended position outward from the housing 260. The sample has been substantially completely moved into the sample vessel 210. This is particularly desirable to improve yield when collecting small sample volumes.

Figure 28:
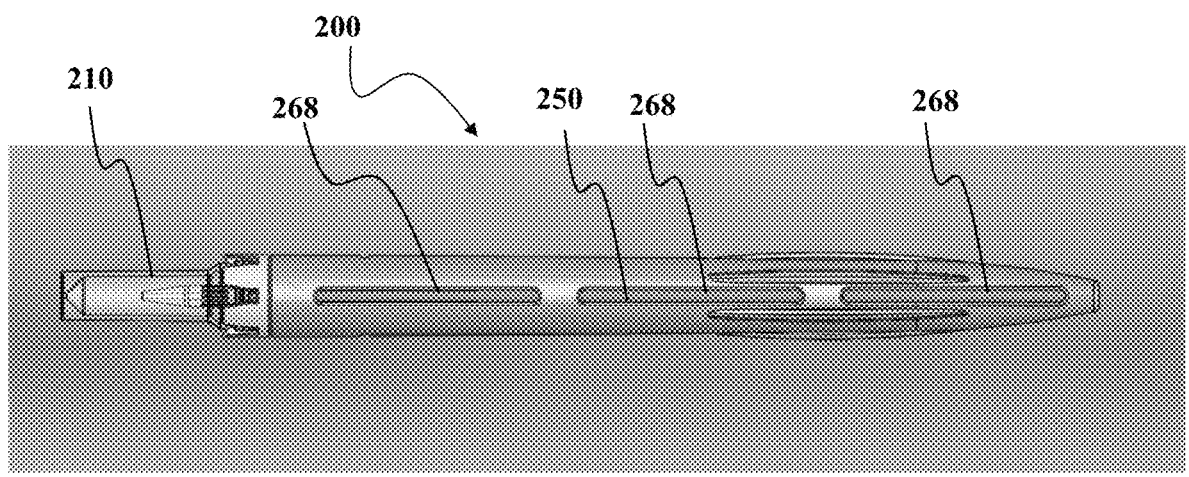
FIG. 28 show a side view of another embodiment of a device as described herein.

Referring now to FIG. 28, a side-view is shown of the device 200. The housing 260 is shown wherein the housing 260 contains visibility windows 268 that allow for visualization of the sample in capillary tube 250 during collection. This visualization can assist the user in confirming that sample is collected knowing when a sufficient amount of sample has be collected in the device. It can also provide feedback to the user to see if they are positioning the sample collection device 200 in the desired position for successful collection, based in part on the rate of sample flow in the capillary tube 250.

Figure 29:
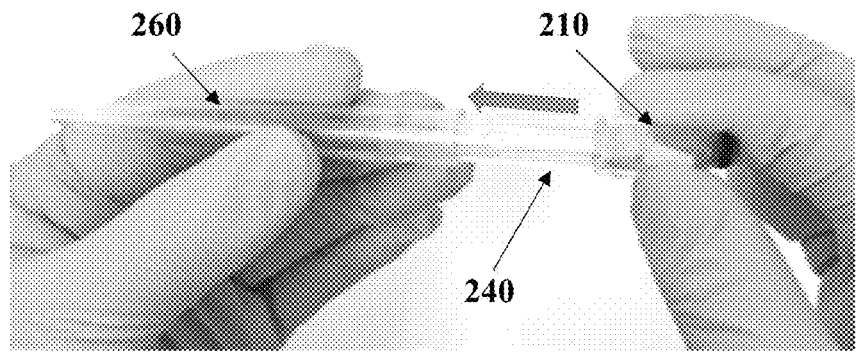
FIGS. 29 to 36 show another non-limiting example of a sequence of steps associated with detaching a sample vessel from one embodiment of a sample collection device.

Referring now to FIGS. 29 to 36, a still further example is provided showing the various steps associated with the use of the sample collection device 200. FIG. 29 shows the sample collection device 200 in a pre-use condition, wherein the sample collection device 200 will be primed by relative motion of sliding a carrier and sample collection device toward the housing 260 as indicated by the arrow.

Figure 30:
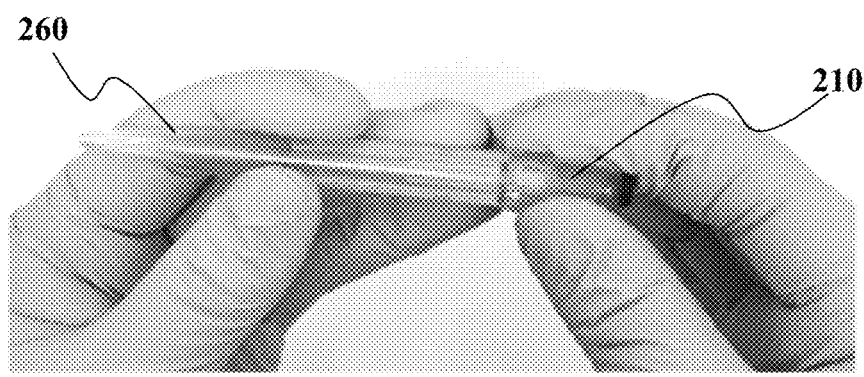

FIG. 30 shows the sample collection device 200 in a primed configuration that is ready to collect sample, wherein the nozzle has pierced the self-healing plug 230.

Figure 31:
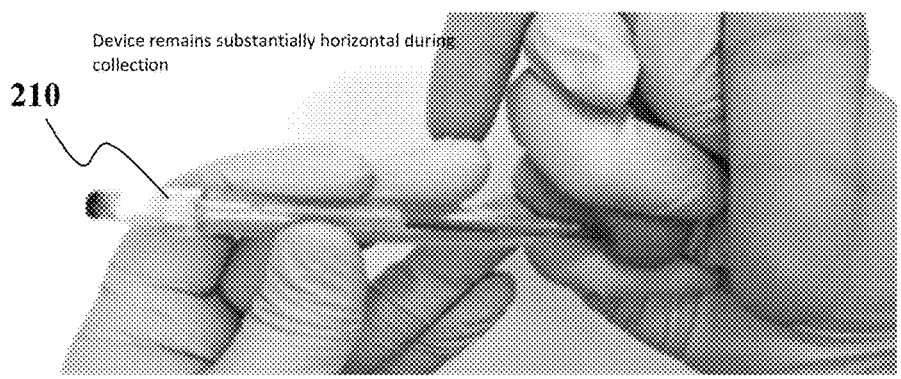

FIG. 31 shows that one end of the sample collection device 200 is touched a pool or droplet of bodily fluid sample. As seen in FIG. 31, the sample collection device 200 is maintained, in this non-limiting example, at a substantially horizontal orientation.

Figure 32:
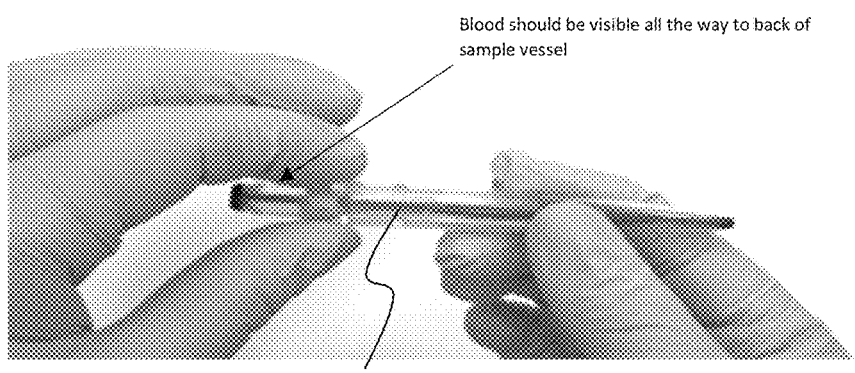

FIG. 32 shows that the sample should be visible all way to the back of the sample collection vessel 210. As seen in FIG. 32, some embodiments may have the entire sample collection device 200 substantially transparent or translucent to better visualize the sample collection process.

Figure 33:
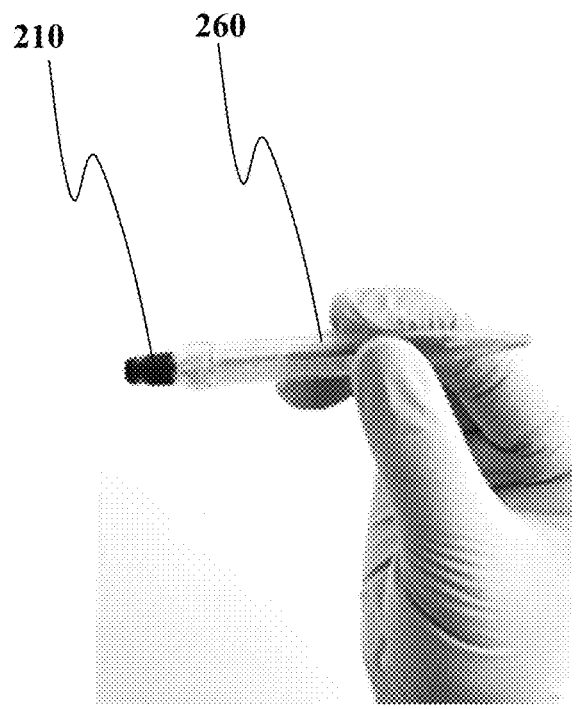
Figure 34:
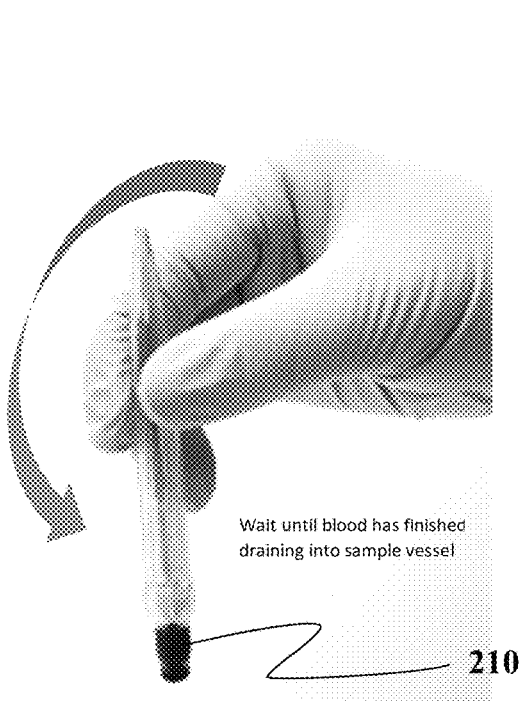

FIGS. 33 and 34 show that the sample collection device 200 is moved from a substantially horizontal orientation to a substantially vertical orientation so that sample in the capillary tube 250 can drain into the sample vessel 210.

Figure 35:
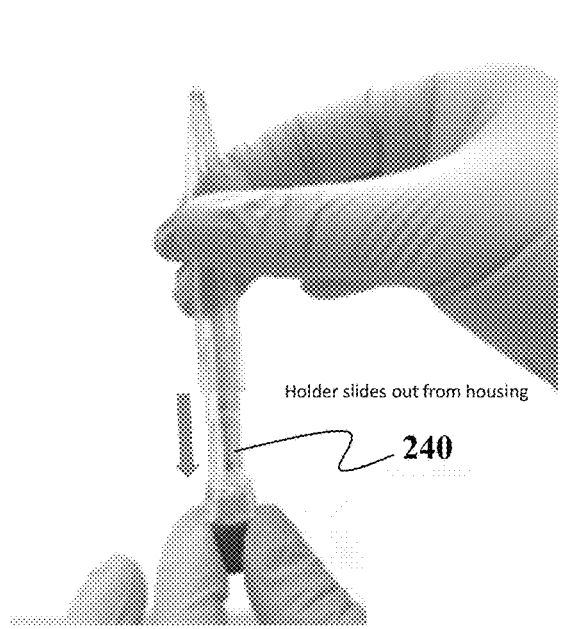

FIG. 35 shows that the guide 240 and sample vessel 210 are extended away from the housing 260 to create a suction effect in the sample vessel 210 to draw residual sample in the capillary tube 250 and the nozzle 220 into the sample vessel 210.

Figure 36:
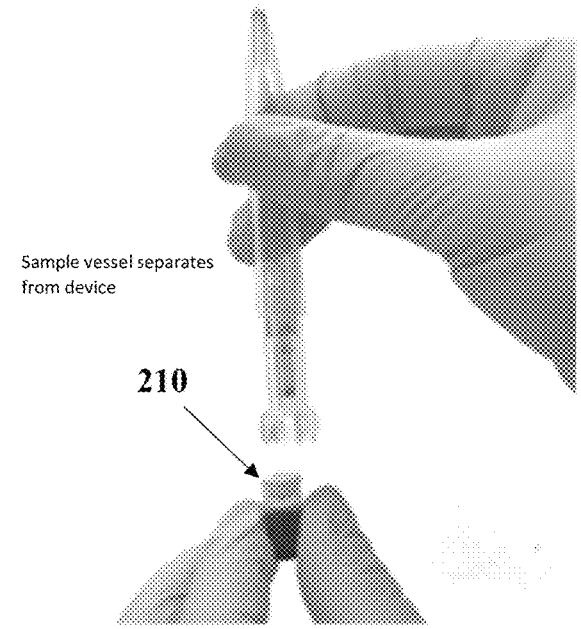

FIG. 36 shows that after residual sample is drawn out from the capillary tube 250 and the nozzle 220, the sample vessel 210 can be detached from the other portions of the sample collection vessel 210. The sample vessel 210 is much smaller than the rest of the collection device 200 and this reduced size facilitates transport and storage of the sample vessel 210 and the sample therein.

Figure 37:
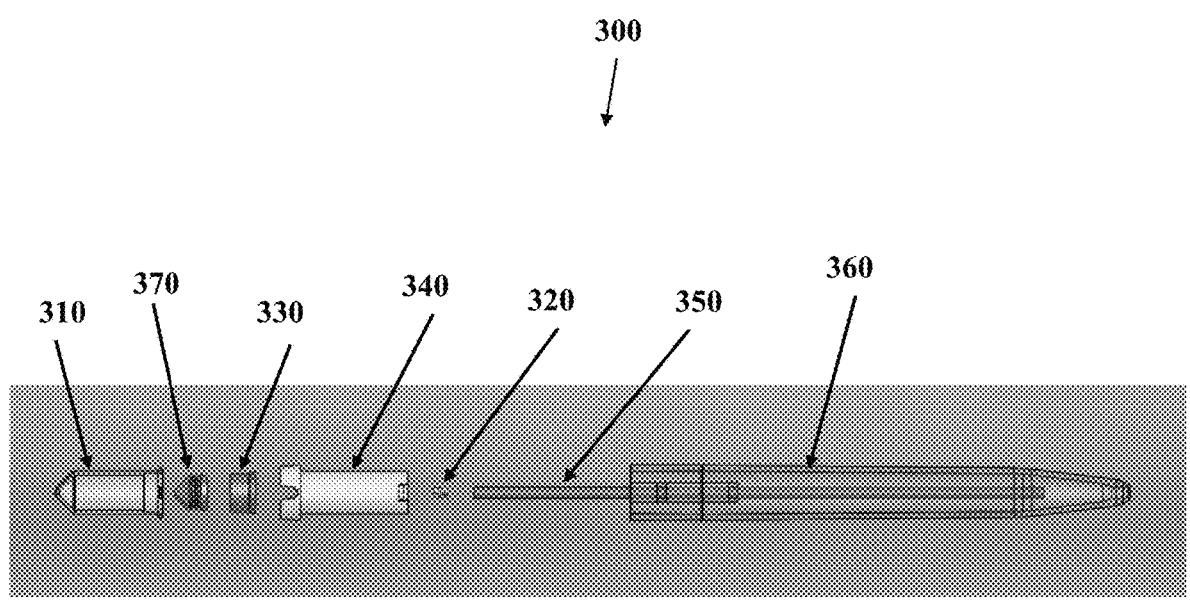
FIG. 37 shows an exploded side view of one embodiment of a device described herein.

Referring now to FIGS. 37 to 41, a still further embodiment of a sample collection device 300 will now be described. FIG. 37 shows that for this embodiment of the sample collection device 300, there is a sample vessel 310, a nozzle 320, a plug 330, a vessel guide 340, a capillary tube 350, and a housing 360. A further feature comprises a vacuum plug 370 located between the vessel 310 and the plug 330. The vacuum plug 370 is designed to work in conjunction with nozzle 320 to create vented and non-vented states.

Figure 38:
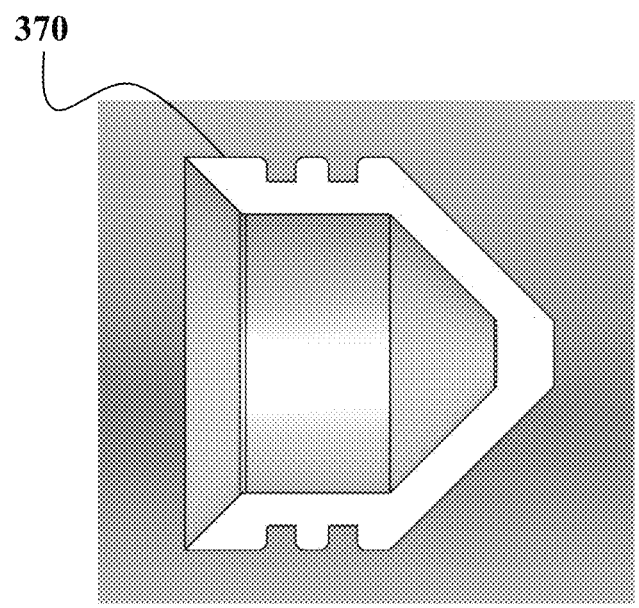
FIGS. 38 to 41 show various perspective views of components associated with the embodiment described in FIG. 37.
Figure 39:
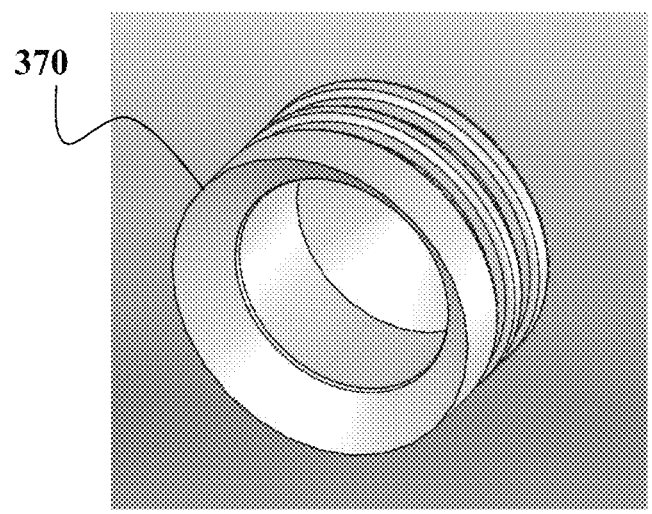

As seen in FIGS. 38 and 39, a vacuum plug 370 is shown in various perspective views.

Figure 40:
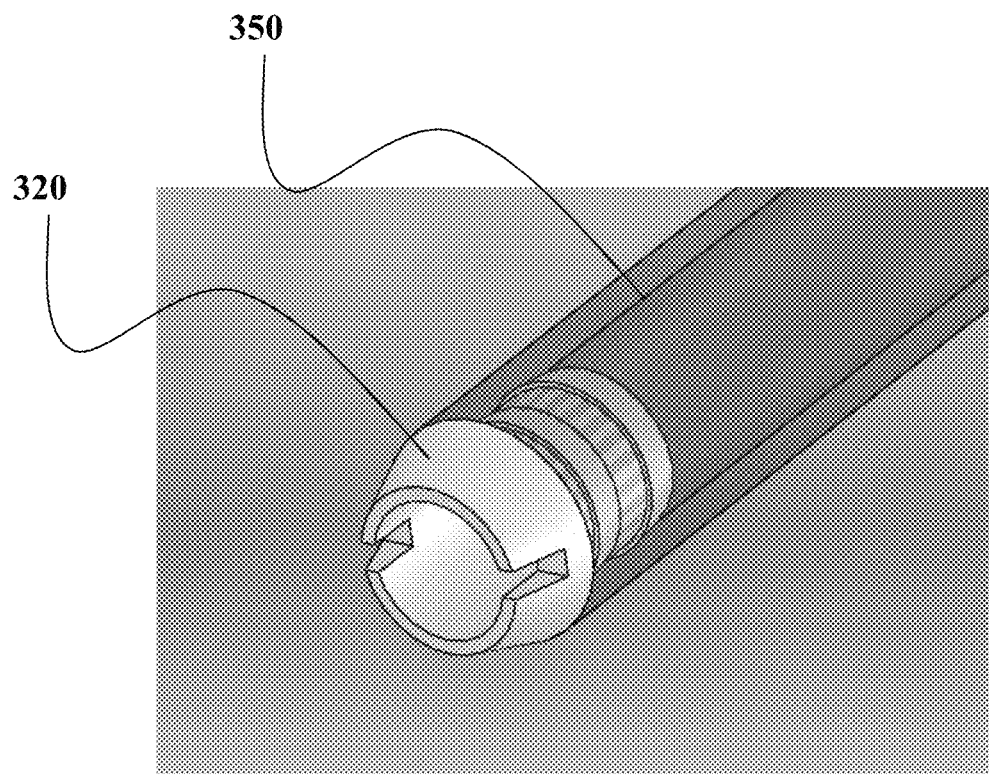
Figure 41:
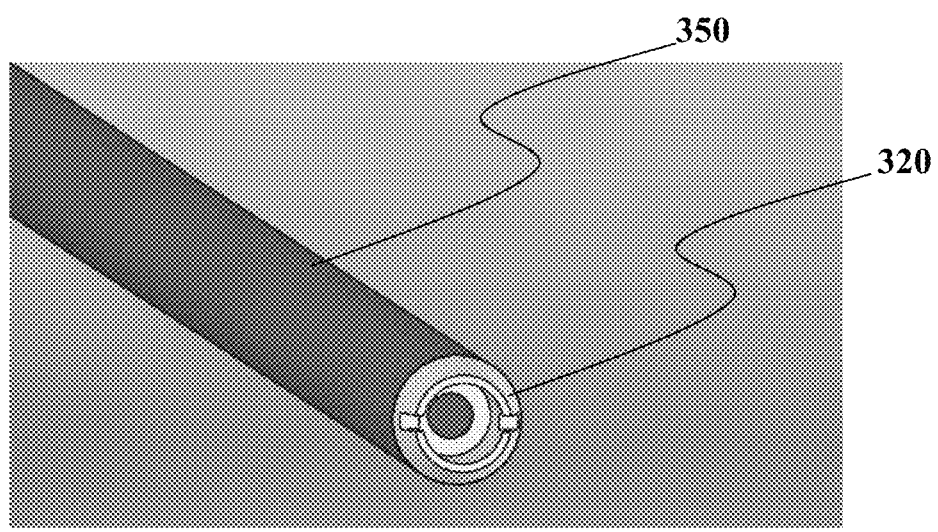

FIGS. 40 and 41 show the nozzle 320 from various perspective views. As seen in FIG. 40, the nozzle 320 may include at least one cut out portion 322 that may facilitate venting through the plug 330.

It should be understood that the nozzle may be injection molded allows for control of flow through the nozzle (mixing, hemolysis, etc.). In at least some embodiments, the system is configured to reduce the chance of contamination outside of vessel (flexible geometry, hydrophobic coatings, etc.).

Referring now to FIGS. 42 and 43, it should be understood that other embodiments may be adapted to use a nozzle or similar sample conduit that has at least one portion that forms a sealed interface at one location but a non-sealed interface at a different location. FIG. 42 shows an embodiment with a single inlet 400 that splits via a Y-shaped tube or channel shape to create two separate paths leading to two separate outlets with nozzles 420 therein for each path. FIG. 43 shows an embodiment with there are two inlets 402 and 404 that create two separate paths leading to two separate outlets with nozzles 420 therein for each path. As seen in FIG. 43, the nozzles 420 may include venting features 422 such as but not limited to the protrusions, channels, or other features the create an imperfect seal with the cap of the sample vessel. It should be understood that other embodiments such as those found in U.S. application Ser. No. 14/320,471 and PCT applications PCT/US13/58627, PCT/US14/30792, PCT/US15/20307, PCT/US13/73443, and PCT/US13/00268, all fully incorporated herein by reference for all purposes. It should be understood that the embodiments creating a vented/unvented condition in one or more sample vessels can be adapted for use with any of the capillary collection devices. It should also be understood that devices used for venous collection blood using a penetrating member such as a needle or lancet can also be configured to use any of the embodiments described herein for creating a vented/unvented condition in one or more sample vessels.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments, it should be understood other sample collection devices can be configured to use the nozzle-guide-plug design set forth herein to extract residual sample into the sample vessel.

Additionally, concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 nm to about 200 nm should be interpreted to include not only the explicitly recited limits of about 1 nm and about 200 nm, but also to include individual sizes such as 2 nm, 3 nm, 4 nm, and sub-ranges such as 10 nm to 50 nm, 20 nm to 100 nm, etc. . . .

The publications discussed or cited herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. All publications mentioned herein are incorporated herein by reference to disclose and describe the structures and/or methods in connection with which the publications are cited. The following application(s) are fully incorporated herein by reference for all purposes: U.S. Provisional Application Ser. No. 62/333,137 filed May 6, 2016.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Any feature, whether preferred or not, may be combined with any other feature, whether preferred or not. The appended claims are not to be interpreted as including means-plus-function limitations, unless such a limitation is explicitly recited in a given claim using the phrase "means for." It should be understood that as used in the description herein and throughout the claims that follow, the meaning of "a," "an," and "the" includes plural reference unless the context clearly dictates otherwise. For example, a reference to "an assay" may refer to a single assay or multiple assays. Also, as used in the description herein and throughout the claims that follow, the meaning of "in" includes "in" and "on" unless the context clearly dictates otherwise. Finally, as used in the description herein and throughout the claims that follow, the meaning of "or" includes both the conjunctive and disjunctive unless the context expressly dictates otherwise. Thus, the term "or" includes "and/or" unless the context expressly dictates otherwise.

What is claimed is:

1. A device comprising:
    at least one capillary tube;
    a nozzle located at a proximal end of the capillary tube;
    at least one collection vessel with a self-healing cap;
    wherein the collection vessel is configured to go from a vented condition, an unvented condition, and then sealed condition as the nozzle is removed from the collection vessel;
    at least one structure on an outer surface of the nozzle wherein when the cap of the at least one collection vessel is configured to slide over said at least one structure, such that the structure is configured to open a vent in the cap and creates said vented condition, wherein said at least one structure is a protrusion, an indentation, a rib, or a bump;
    wherein during nozzle removal when any venting of the collection vessel is sealed, continued pulling of the collection vessel provides for vacuum force to be created within the collection vessel,
    wherein during removal, the nozzle enters into a non-vented state which then allows for creation of a vacuum in the collection vessel which in turn is configured to pull sample into the collection vessel;
    wherein the collection vessel is configured to move relative to the capillary tube and said collection vessel is detachable from the device.

2. A device comprising:
at least one sample collection channel;
at least one collection vessel with a cap;
at least one structure on an outer surface of the sample collection channel, wherein when the cap of the collection vessel is configured to slide over said at least one structure, such that the at least one structure is configured to open a vent in the cap and creates a vented configuration, wherein said at least one structure is a protrusion, an indentation, a rib, or a bump;
wherein the collection vessel is configured to go from said vented configuration, to an unvented configuration, and then sealed configuration as the collection vessel is moved along a path to disengage from the sample collection channel;
wherein the collection vessel is configured to be movable relative to the sample collection channel and said collection vessel is detachable from the device.

3. A method comprising:
providing a sample collection device comprising at least one sample collection channel and at least one collection vessel coupled to receive sample from the sample collection channel, wherein said collection vessel comprises a cap and said sample collection channel comprises at least one structure on an outer surface of the sample collection channel, wherein said at least one structure is a protrusion, an indentation, a rib, or a bump;
wherein the cap of the collection vessel slides over said at least one structure, to open a vent in the cap and create a vented condition;
wherein the collection vessel is configured to go from said vented condition, to an unvented condition, and then sealed condition as the collection vessel is moved along a path to disengage from the sample collection channel;
wherein the collection vessel is configured to be movable relative to the sample collection channel and said collection vessel is detachable from the sample collection device.

4. The device of claim 1 wherein a suction effect is created by the nozzle forming a seal with the self-healing cap.

5. The device of claim 1 wherein the collection vessel is transparent.

6. The device of claim 1 wherein the collection vessel is translucent.

7. The device of claim 1 wherein the collection vessel comprises an optically transmissive material.

8. The device of claim 1 wherein the collection vessel is coated with an anticoagulant.

9. The device of claim 1 wherein the capillary tube is coated with an anticoagulant.

10. The device of claim 2 wherein the collection channel is coated with an anticoagulant.

11. The device of claim 2 wherein the collection vessel is coated with an anticoagulant.

12. The method of claim 3 wherein the sample collection channel is coated with an anticoagulant.

13. The method of claim 3 wherein the collection vessel is coated with an anticoagulant.

\* \* \* \* \*